United States Patent
Henderson et al.

(10) Patent No.: US 10,368,993 B2
(45) Date of Patent: Aug. 6, 2019

(54) SHAPE-MEMORY-ACTUATED MATERIALS FOR ACCELERATED HEALING OF ORTHOPEDIC INJURIES

(71) Applicants: James Henderson, Syracuse, NY (US); Patrick T. Mather, Oxford, PA (US)

(72) Inventors: James Henderson, Syracuse, NY (US); Patrick T. Mather, Oxford, PA (US)

(73) Assignee: Syracuse University, Syracuse, NY (US)

(*) Notice: Subject to any disclaimer, the term of this patent is extended or adjusted under 35 U.S.C. 154(b) by 0 days.

(21) Appl. No.: 15/648,721

(22) Filed: Jul. 13, 2017

(65) Prior Publication Data

US 2017/0312082 A1  Nov. 2, 2017

Related U.S. Application Data

(62) Division of application No. 14/899,316, filed as application No. PCT/US2014/043327 on Jun. 20, 2014, now Pat. No. 9,744,041.

(60) Provisional application No. 61/837,226, filed on Jun. 20, 2013.

(51) Int. Cl.

| | |
|---|---|
| *A61F 2/28* | (2006.01) |
| *A61L 27/14* | (2006.01) |
| *A61L 27/56* | (2006.01) |
| *A61L 27/50* | (2006.01) |
| *A61L 27/16* | (2006.01) |
| *A61L 27/18* | (2006.01) |
| *A61L 27/38* | (2006.01) |
| *A61F 2/30* | (2006.01) |

(52) U.S. Cl.
CPC .............. *A61F 2/2846* (2013.01); *A61F 2/28* (2013.01); *A61L 27/14* (2013.01); *A61L 27/16* (2013.01); *A61L 27/18* (2013.01); *A61L 27/3847* (2013.01); *A61L 27/50* (2013.01); *A61L 27/56* (2013.01); *A61F 2002/285* (2013.01); *A61F 2002/2817* (2013.01); *A61F 2002/2839* (2013.01); *A61F 2002/30092* (2013.01); *A61F 2210/0014* (2013.01); *A61L 2400/16* (2013.01); *A61L 2430/02* (2013.01)

(58) Field of Classification Search
CPC .............. A61F 2/2846; A61F 2002/285; A61F 2002/2817; A61F 2002/2839; A61F 2002/30092; A61F 2210/0014; A61L 27/3847; A61L 27/3852
See application file for complete search history.

(56) References Cited

U.S. PATENT DOCUMENTS

2012/0095463 A1* 4/2012 Rains ..................... A61B 17/72
606/63

* cited by examiner

*Primary Examiner* — Christopher D. Prone
(74) *Attorney, Agent, or Firm* — Bond Schoeneck and King PLLC; George McGuire

(57) ABSTRACT

A three component system for repairing critically sized bone defects having a first shape memory polymer (SMP) component formed as a scaffold that fills the defects, a second SMP component formed as a restricting sleeve that stabilizes and supports osseointegration and osteoconduction, and a third SMP component formed as a two-dimensional cell culture substrate for engineering periosteal grafts.

6 Claims, 16 Drawing Sheets

SHAPE-MEMORY-ACTUATED MATERIALS FOR ACCELERATED HEALING OF ORTHOPEDIC INJURIES

CROSS-REFERENCE TO RELATED APPLICATIONS

The present application is a divisional of U.S. application Ser. No. 14/899,316, filed on Dec. 17, 2015, which was a national stage application of PCT/US14/43327 filed on Jun. 20, 2014, which claimed priority to U.S. Provisional Application No. 61/837,226, filed on Jun. 20, 2013.

STATEMENT REGARDING FEDERALLY SPONSORED RESEARCH OR DEVELOPMENT

This invention was made with government support under D12AP00271 awarded by Defense Advanced Research Projects Agency (DARPA). The government has certain rights in the invention.

BACKGROUND OF THE INVENTION

1. Field of the Invention

The present invention relates to bone substitutes and, more particularly, to a shape memory polymer system for repairing bone defects.

2. Description of the Related Art

The nature of modern insurgency warfare combined with improved survival rates due to advances in body armor has created increasingly complex challenges for orthopedic reconstruction of extremity injuries in warfighters. More than 70% of military-related extremity fractures now involve massive bone loss, termed critically sized defects. Current grafting options for these defects have important limitations, described below. Additionally, for some combat-related critically sized defects there are no reliable treatments, and more than 7% of severe extremity injuries result in major amputation. There is a need for revolutionary functional materials that significantly improve control of graft integration (osseointegration) and bone formation (osteogenesis) during repair of critically sized defects.

To repair critically sized defects in the extremities of warfighters, live autograft—bone harvested from the same patient—remains the gold standard for small defects. But autologous bone is not always an option, particularly when multiple-limb trauma occurs within the same patient or when the defect is too large. Furthermore, complications include pain, infection, donor site morbidity, and inefficient repair due to limited osseointegration and remodeling. Allograft—bone harvested from a donor—provides the best current alternative, but often achieves limited osseointegration with a failure rate of 60% at 10 years. Synthetic bone graft substitutes have been developed and have generally been calcium phosphate or calcium sulfate space fillers or cements. Like allografts, synthetic bone graft substitutes lack living cells and function only as a scaffold for bone ingrowth (osteoconduction). Moreover, compared to auto- or allograft, synthetic grafts possess inferior mechanical strength and fracture resistance, preventing use in large defects that require rapid loadbearing capabilities. Graft approaches are often further complicated by damage to the periosteum—the tissue that covers the outer surface of bone and is critical to graft healing and remodeling.

In addition to the challenges listed above, information from major military medical institutions indicates that a subset of defects cannot be managed well with any existing treatment. Segmental defects—in which a segment of bone is missing and there is no continuity of bone within the fracture—are a particular problem. There is, therefore, an unmet need for highly effective bone substitutes. Ideally, these substitutes would conform to the defect, rapidly achieve mechanical properties similar to bone, integrate with neighboring bone, and support osteoconduction and remodeling.

BRIEF SUMMARY OF THE INVENTION

The present invention comprises a system of shape memory polymer (SMP) materials that, together, enable repair of critically sized bone defects via three essential and co-dependent steps, namely: (1) filling of critically sized defects, (2) stabilization and support of osseointegration and osteoconduction, and (3) engineering of periosteal grafts that support osteogenesis and remodeling. The first component is an SMP scaffold that can undergo programmed expansion under simulated physiological conditions. The scaffold can easily be manipulated by hand to fit within a bone defect and, once in situ, can expand to conform to the shape of the defect for the purpose of quickly integrating with and providing mechanical properties comparable to native bone while supporting osteoconduction and remodeling. For example, the scaffold can use an end-linked co-network consisting of poly(ethylene oxide) and poly (epsilon-caprolactone) diene chains linked together into a well-defined covalent network through photoinitiated addition of the vinyl termini with a multifunctional thiol cross-linker.

The second component is an SMP sleeve that can undergo programmed radial contraction under simulated physiological conditions. The osteoconductive biomaterial sleeve employs SMP functionality to contract for the purpose of stabilizing a defect site while concurrently promoting healing as a biomimetic periosteum. The sleeve uses a thermoplastic polyurethane.

The third component is a two-dimensional cell culture substrate that can undergo programmed expansion or a change in topography for mechanobiological engineering of periosteal sheets in vitro. The two-dimensional SMP substrate employs shape-memory expansion or shape-memory actuated change in topography to provide biomimetic biomechanical stimulation to stem cells during engineering of periosteal sheets in vitro. The substrates uses a co-polymer system incorporating the monomers tert-butyl acrylate and butyl acrylate, but the technology is not limited to this particular monomer system.

The present invention thus provides a coordinated system of orthopaedic smart materials that a military or civilian trauma surgeon or orthopaedic surgeon (the end user) can use to treat critically sized defects. This technology will provide surgeons with a new option in cases where suitable treatment options have not previously existed, thereby reducing the number of cases that result in amputation. In addition, the technology will provide surgeon with an approach that allows treatment via a single surgery, thereby avoiding the need for multiple revision surgeries, which are often required with current approaches. Furthermore, the resorbable and biodegradable design of the technology avoids complications, such as corrosion and local and systemic infection and cytotoxicity, commonly associated with metal hardware used in many current treatment options.

Further applications of the technology include adaptation of the system to treatment of injuries and diseases in both other areas of the musculoskeletal systems and in other organ systems. In addition, the system can be scaled for use by veterinarians in animals.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 1 is a schematic of a three component system, including a Scaffold that can undergo programmed expansion to conform to the shape of a bone defect and support osteoconduction and remodeling, an osteoconductive sleeve that can undergo programmed radial contraction to stabilize a defect site and promoting healing, and two-dimensional cell culture substrate that can undergo programmed expansion or topographic change to provide biomimetic biomechanical stimulation to stem cells during engineering of periosteal sheets for use as periosteal grafts;

Figure 7:
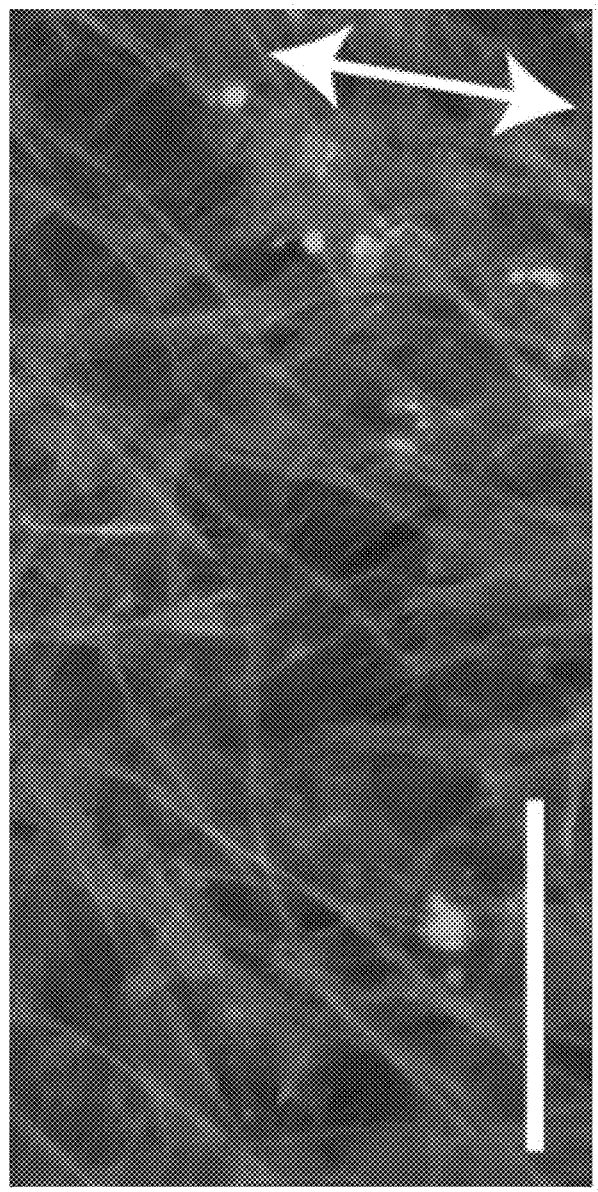
Figure 8:
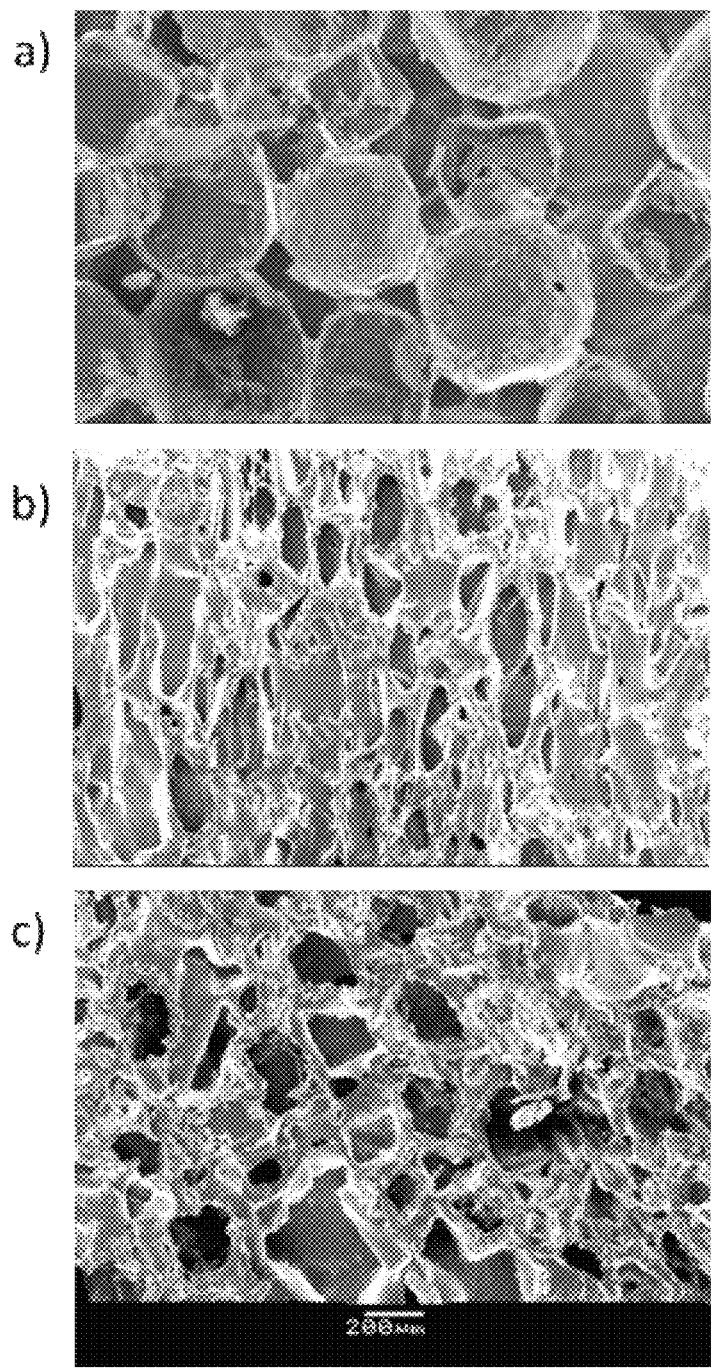
Figure 9:
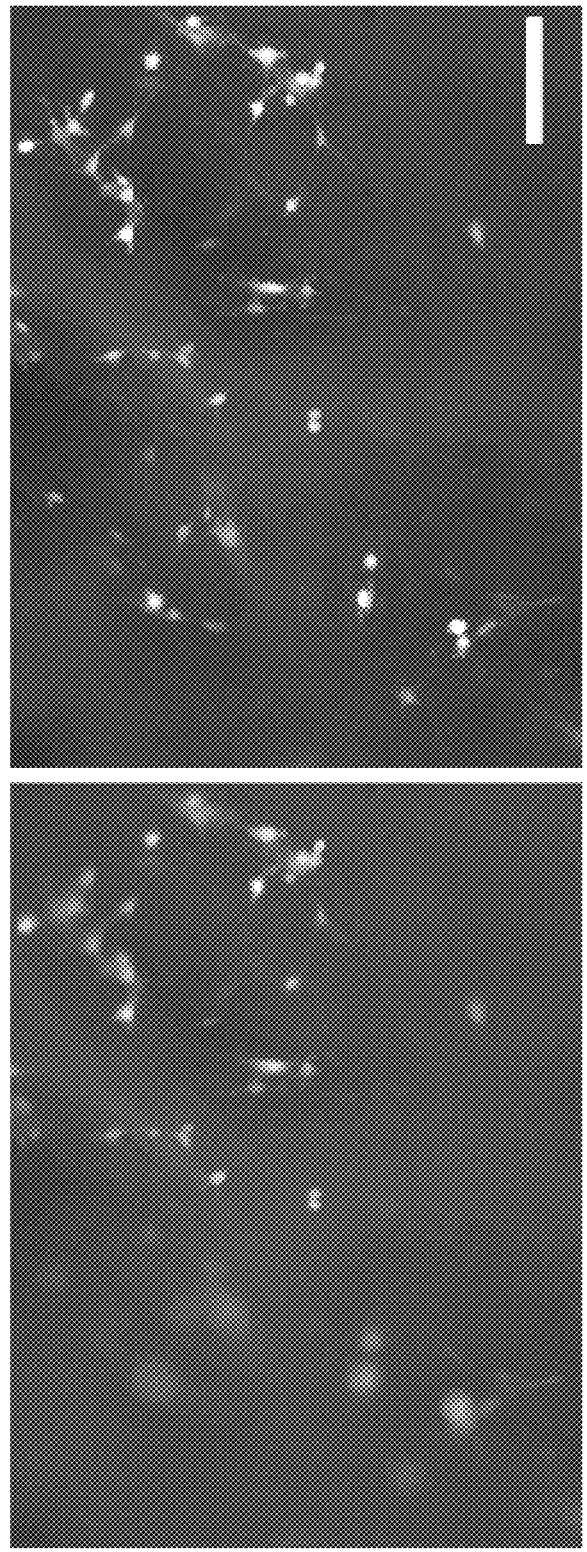
Figure 10:
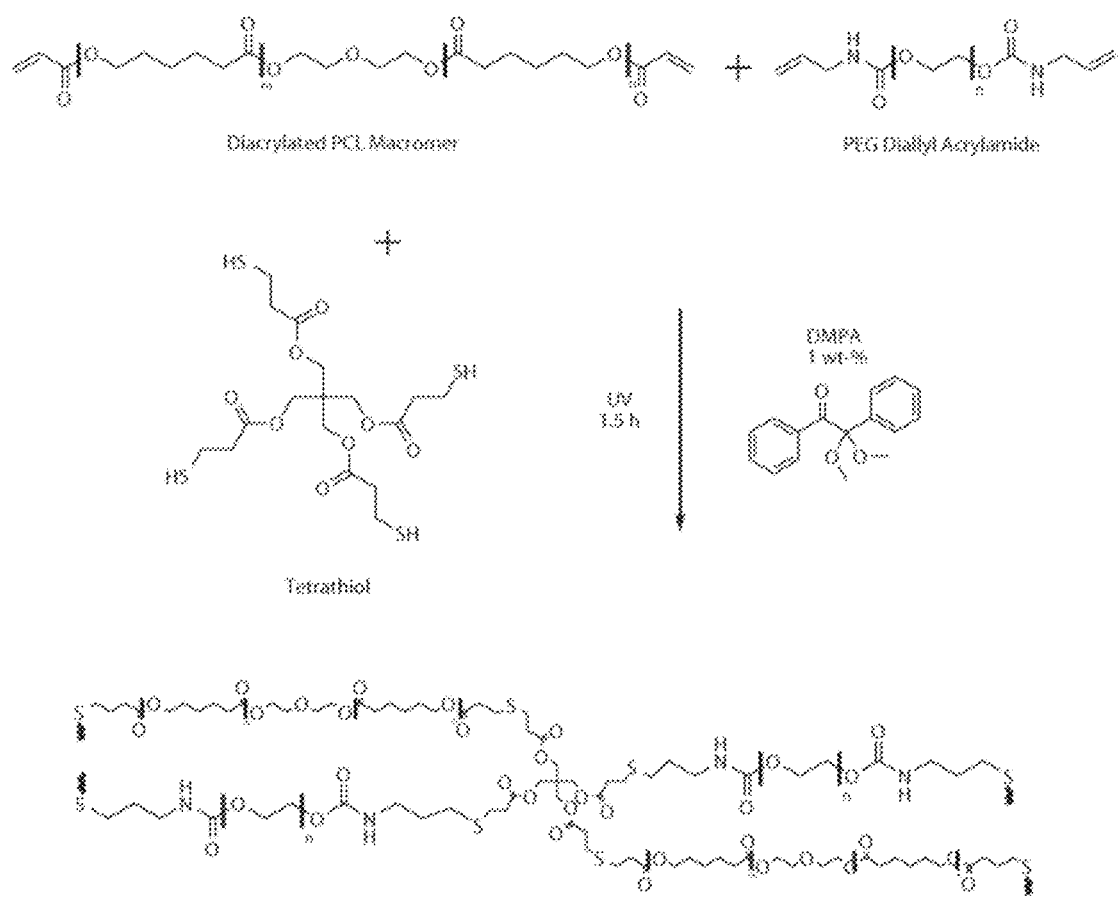
Figure 11:
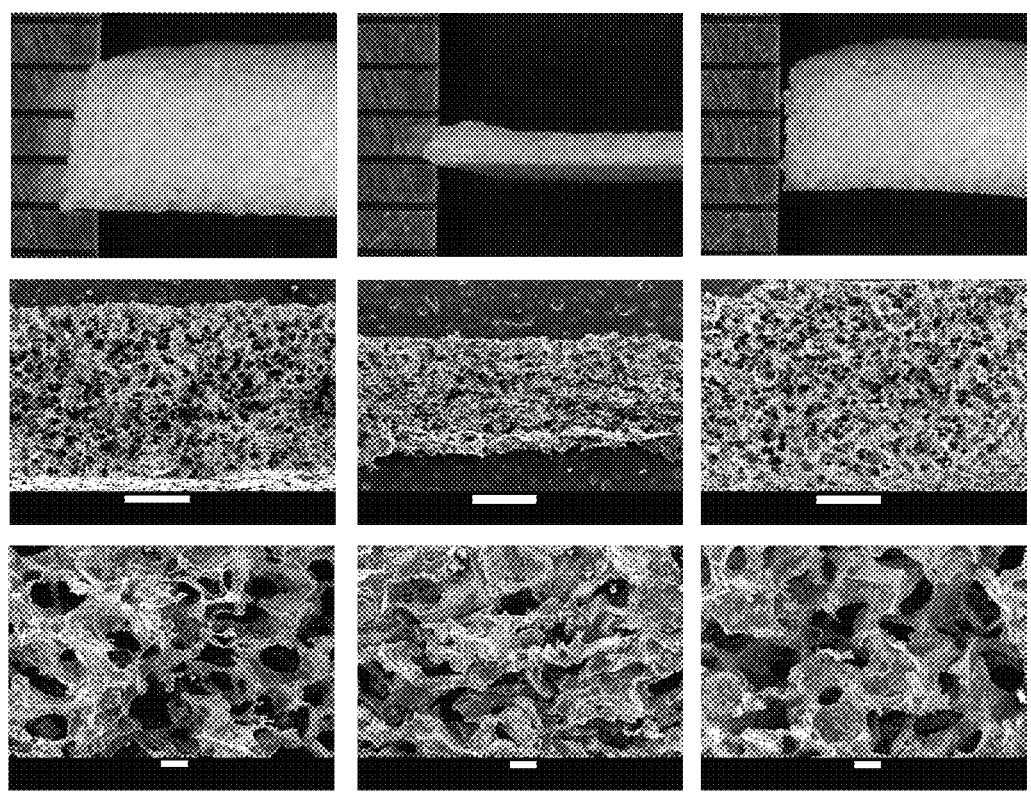
Figure 12:
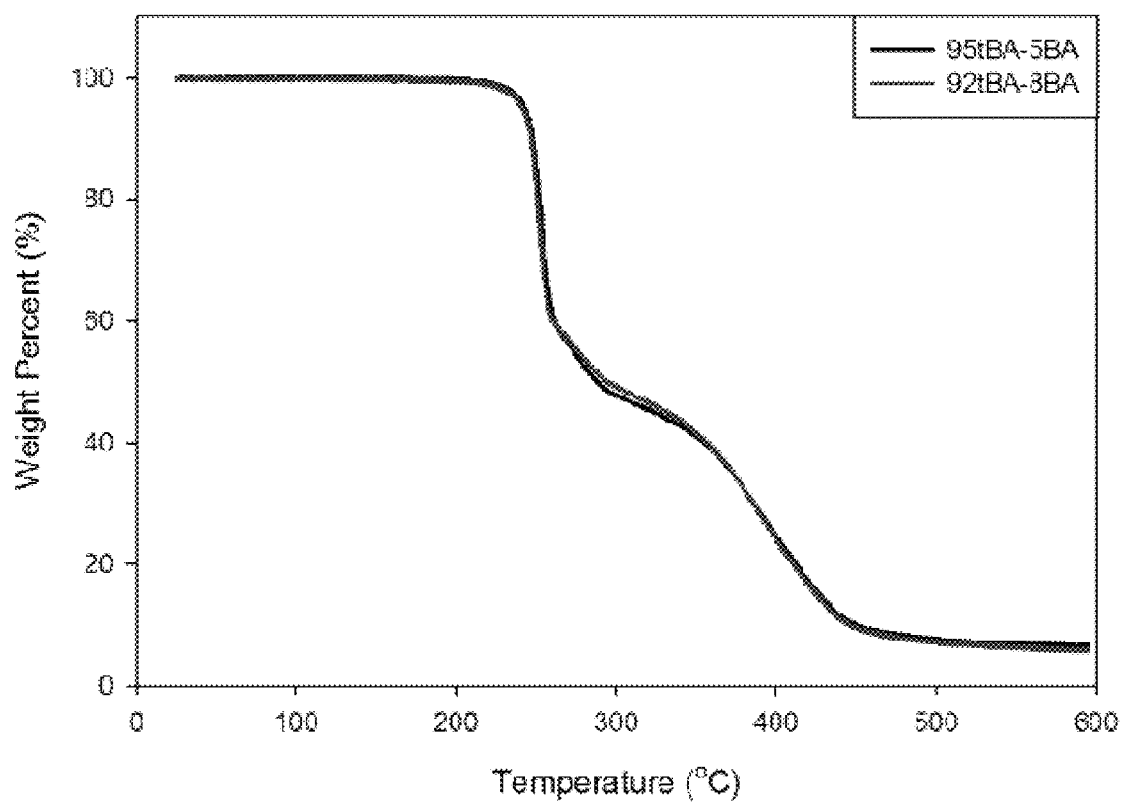
Figure 13A:
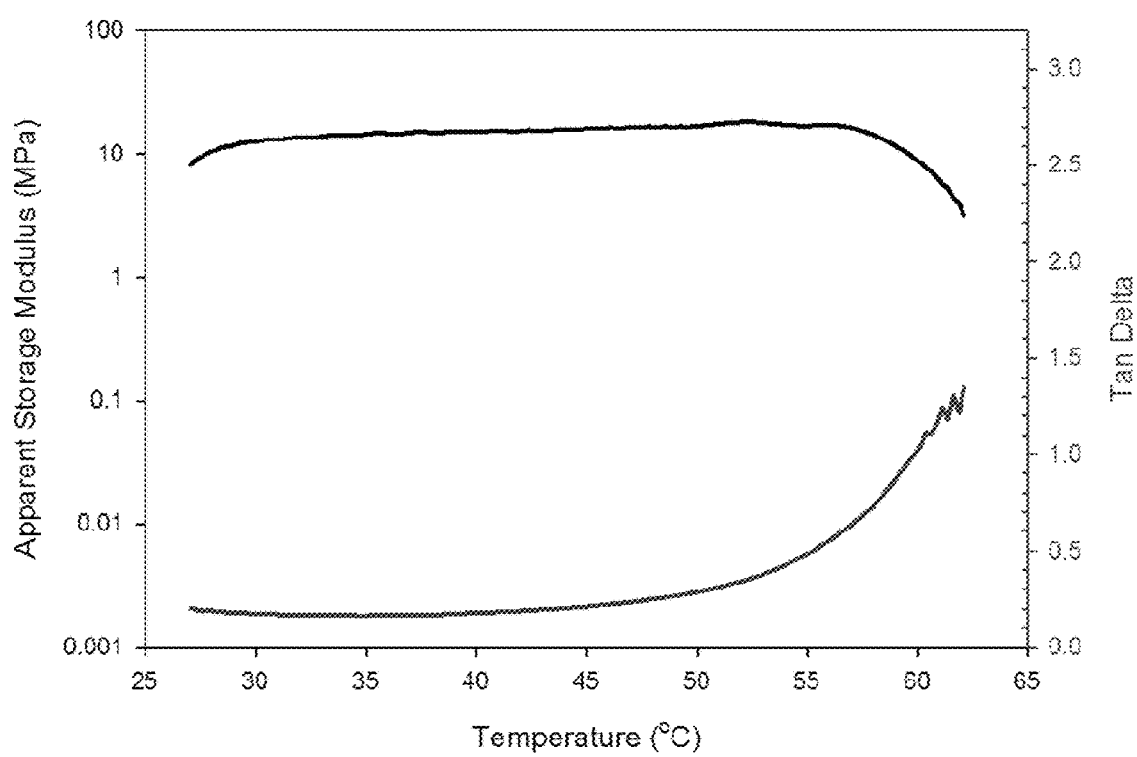
Figure 13B:
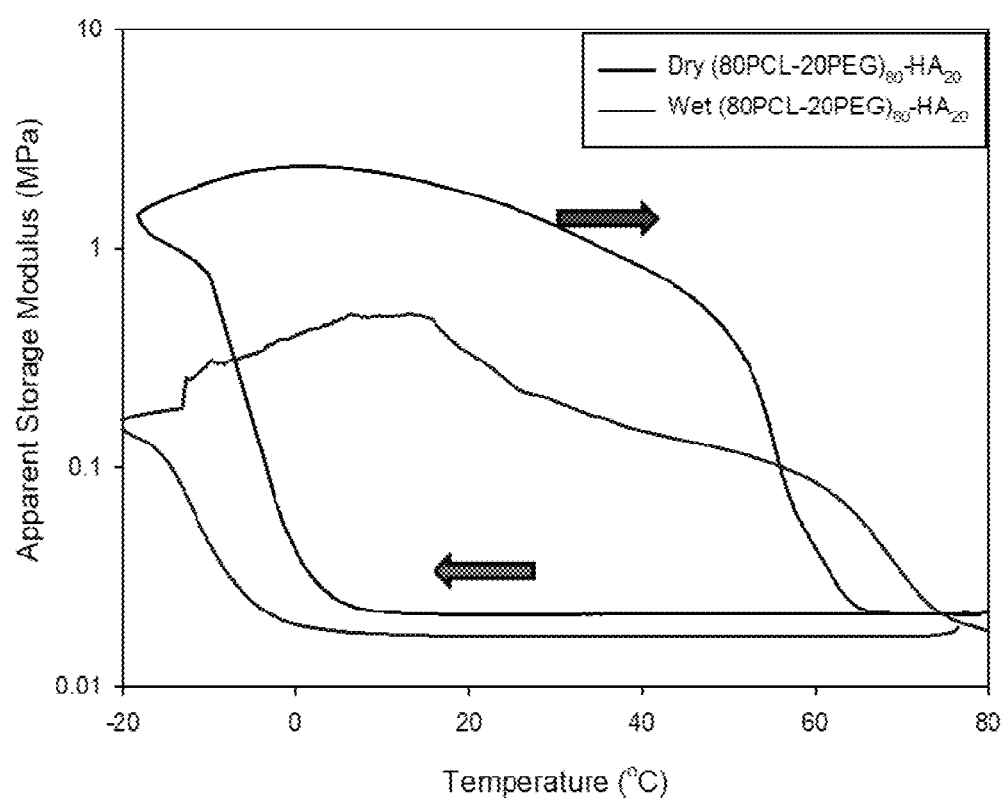
Figure 14:
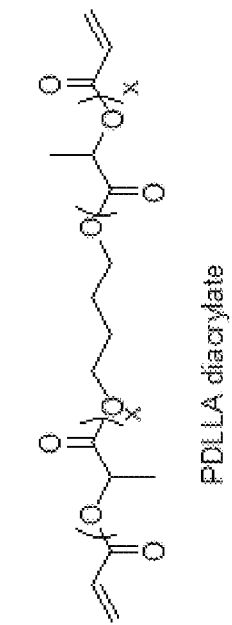
Figure 14:
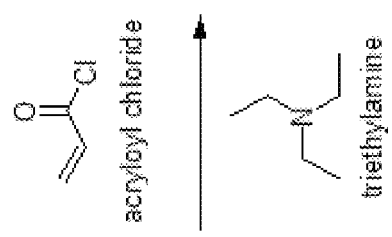
Figure 14:
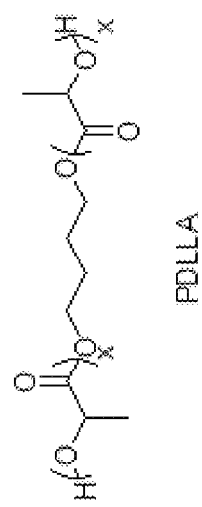

FIG. 7 is an image of a sheet of mouse C3H/10T1/2 progenitor cells being cultured under a gradient of tension on an expanding SMP substrate, and are shown after 13 h of substrate expansion following triggering by slight heating from 30 to 37° C., with a max strain if 8.1%, the approximate direction of expansion indicated by the double-headed arrow, and phalloidin (green) staining of filamentous actin and SYTOX (blue) staining of nuclei, where the scale bar is 100 μm;

FIG. 8 is a series of scanning electron micrographs of the top surface of a PCL scaffold (a) before fixing, (b) after fixing, and (c) after recovery;

FIG. 9 is a series of images of a LIVE/DEAD assay performed on cells seeded on a scaffold with a pore size of 200-500 μm, with (left) cells in a single focal plane and a (right) z-stack projection of 120 μm showing cells from multiple focal planes (scale bar 200 μm), where green cells stain viable cells, while red cells depict dead cells;

FIG. 10 is a schematic of SMP network formation using photo-initiated addition reactions between oligomeric macromers and the shown tetrathiol;

FIG. 11 is a series of images showing compressive shape memory behavior and effect on pore morphology, with compressive shape memory (left) before compression, (middle) after compression and fixing, and (right) after recovery show that the SMP scaffold is able to fully recover back to the original state and restore its porous architecture, where scale bars: 1 mm (middle row) and 100 μm (bottom row);

FIG. 12 is a graph of the thermogravimetric analysis of 92tBA-8BA foams according to the present invention;

FIGS. 13A and 13B are graphs of the storage modulus sweep for 92tBA-8BA foams and 80PCL-20PEG foams, respectively;

FIG. 14 is a schematic of the formation of a PDLLA diacrylate; and

Figure 15:
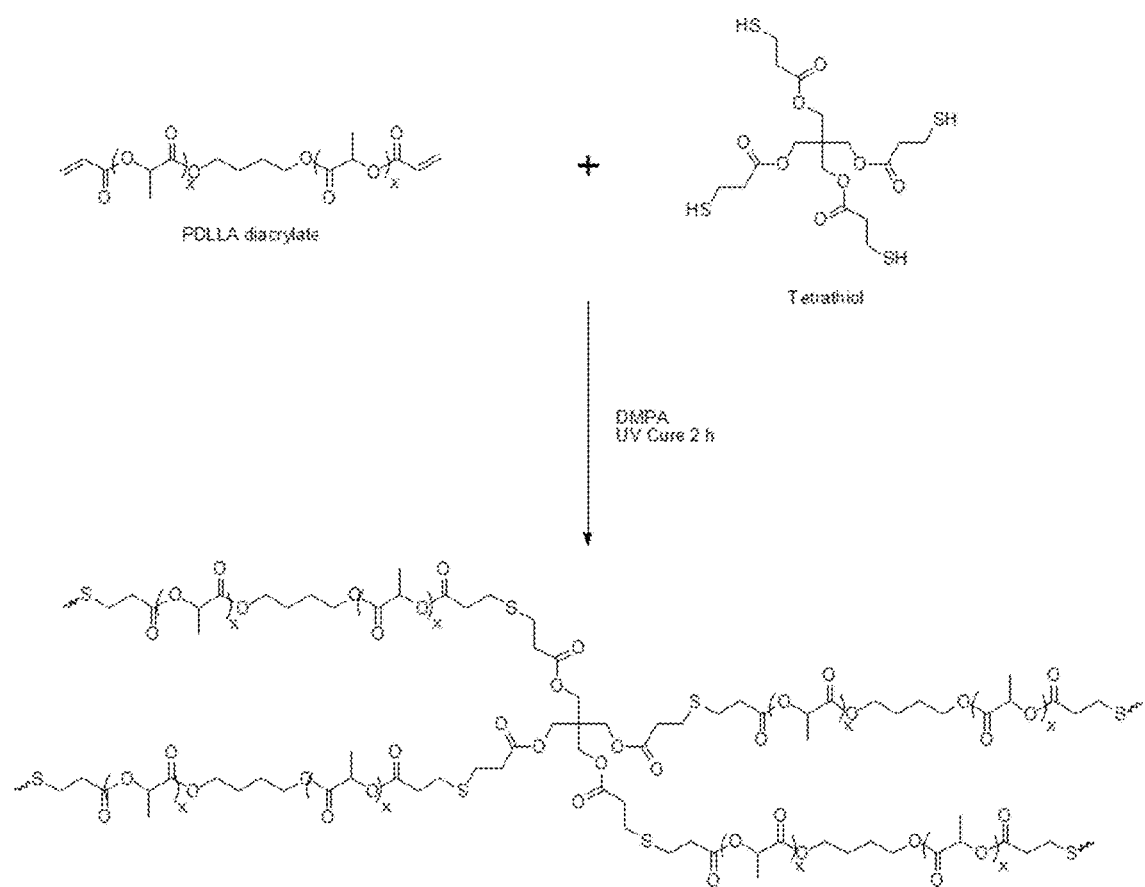
Figure 16:
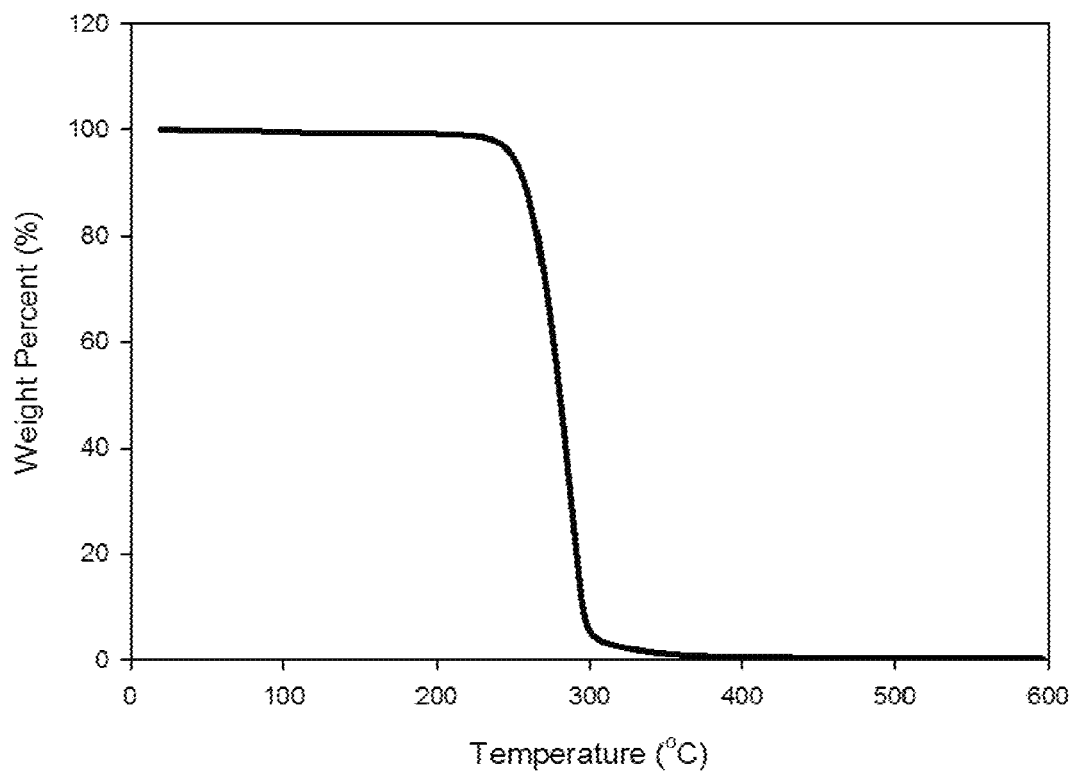

FIG. 15 is a schematic of the cross-linking of the functionalized PDLLA diacrylate of FIG. 14 with tetrathiol via UV polymerization;

FIG. 16 is a graph of the thermogravimetric analysis of PDLLA_POSS_34k; and

Figure 17:
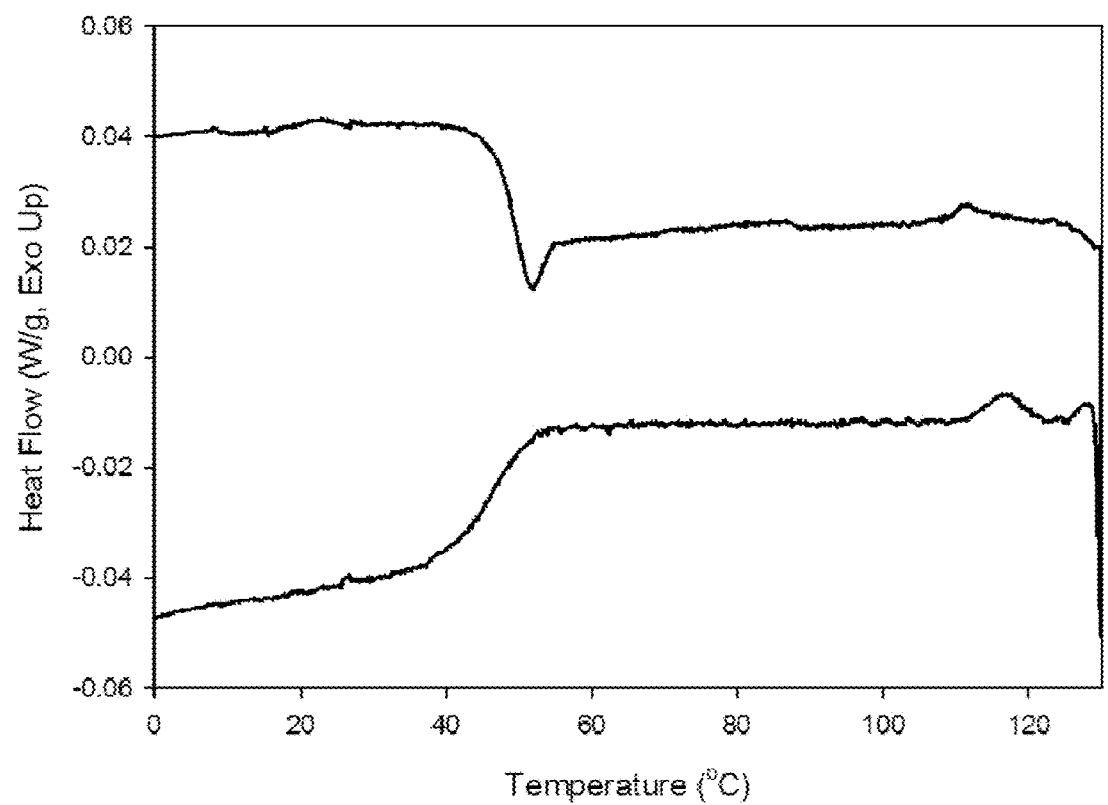

FIG. 17 is a graph of the second heating trace and first cooling trace of PDLLA_POSS_34k.

DETAILED DESCRIPTION OF THE INVENTION

Figure 1:
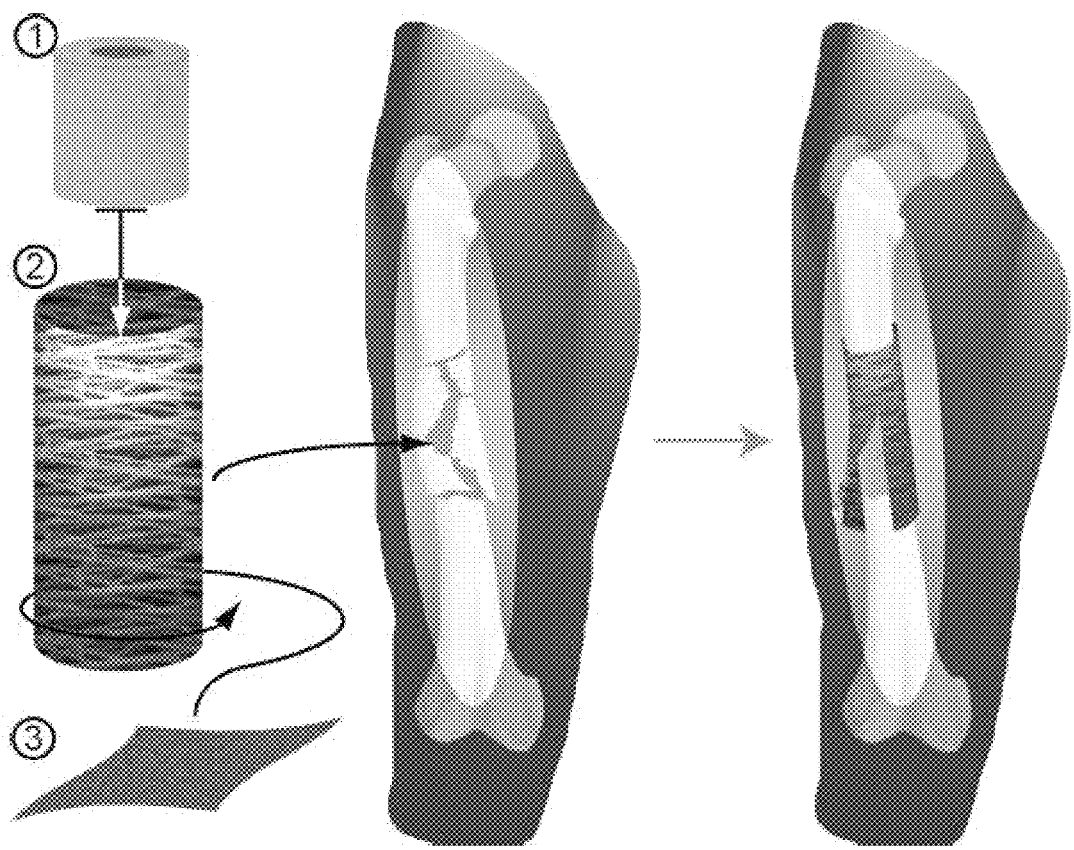

Referring now to the drawings, wherein like reference numerals refer to like parts throughout, there is seen in FIG. 1 a three component system of shape memory polymer (SMP) materials according to the present invention that, together, enable repair of critically sized bone defects by filling critically sized defects, providing stabilization and support of osseointegration and osteoconduction, and allowing engineering of periosteal grafts that support osteogenesis and remodeling. However, it is also possible for the three components of the present invention to be used individually, or in sub-combinations, depending on the injury and extent of bone loss.

Figure 2:
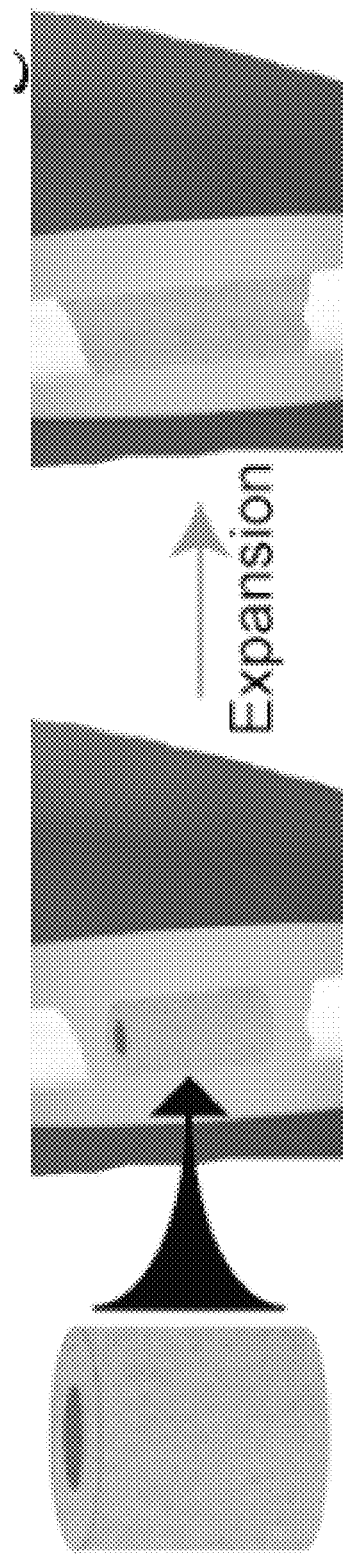
FIG. 2 is a schematic of a scaffold according to the present invention that can undergo programmed expansion to conform to defect shape and to support osteoconduction and remodeling.
Figure 3:
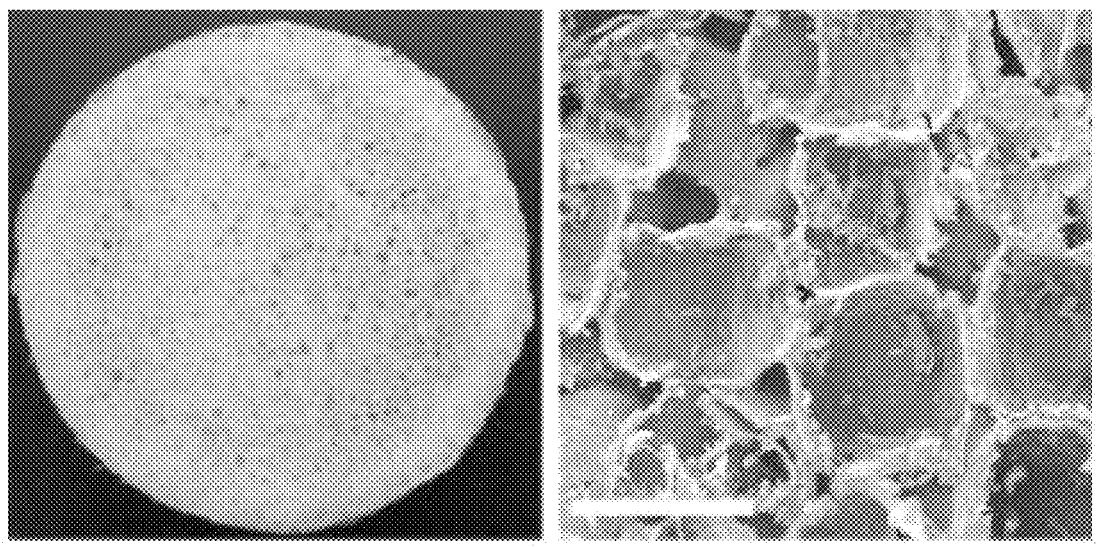
FIG. 3 is a series of images of a SMP foam prepared according to the present invention from end-linked poly(ε-caprolactone) using salt leaching, where the disk is 25 mm in diameter and the SEM scale bar is 500 μm.

The first component of the present invention is an SMP scaffold 1 that can undergo programmed expansion under simulated physiological conditions. Referring to FIG. 2, the scaffold can easily be manipulated by hand to fit within a bone defect and, once in situ, can expand to conform to the shape of the defect for the purpose of quickly integrating with and providing mechanical properties comparable to native bone while supporting osteoconduction and remodeling. Preferably, the first component according to the present invention uses temperature-, hydration-, or degradation-actuated changes in shape to develop a porous foam scaffold that can be programmed to expand under physiological conditions. The rationale for this approach is that expansion will allow the scaffold to conform to a defect and will result in high porosity, facilitating osteoconduction. Use of a semi-rigid scaffold, rather than a hydrogel as in conventional approaches, will enable rapid achievement of functional mechanical properties, allowing rapid resumption of load-bearing and speeding healing and remodeling. In a preferred embodiment, this aspect of the present invention is formed from a single polymer family: an end-linked co-networks consisting of poly(ethylene oxide) and poly(ε-caprolactone) diene chains linked together into a well-defined covalent network through photo-initiated addition of the vinyl termini with a multifunctional thiol crosslinker. This polymer family may be tailored for application as a bone graft substitute with structural actuation by slight heating, water plasticization, polymer degradation, or some combination of the three. Furthermore, the end-linking chemistry can be modified to include urethane bond formation by functionalizing the macromer chains described above with either isocyanate or alcohol groups and crosslinking with a multifunctional, complementary crosslinker bearing alcohol or isocyanate groups, respectively, and using a suitable catalyst from among many known in the art. Similarly, the end-linking chemistry can be modified to include alkyne-azide "click" chemistry by functionalizing the macromer chains described above with either alkyne or azide groups and crosslinking with a multifunctional, complementary crosslinker bearing azide or alkyne groups, respectively, and using a suitable catalyst known in the art. Standard methods of polymer science (e.g., x-ray, calorimetry, and microtensile testing) may be applied to ascertain structure-property relations that guide refined materials design. Porous foams may be formed by salt leaching, such as end-linked PCL networks with 10% polymer density, as seen in FIG. 3.

To modulate cell adhesion on such scaffolds, an RGD-bearing network chain was employed, which has proven effective in companion work on shape memory hydrogels. In addition, nano-hydroxyapatite (HA) incorporation into the scaffold may increase cell adhesion and mineralization. Scaffold storage modulus increased with HA content while the degree of shape-memory recovery decreased, as would be expected. Conformation of the scaffold to a defect may be simulated using circular or irregular holes punched in high-HA-content PCL films, with assessment of anchoring using push-out tests. Minimally invasive delivery may be simulated by passing scaffolds through a 10 mm ID laparoscopic tube into 37° C. culture medium, followed by analysis of recovery. Osteoconductive capacity may be assessed by histology and quantitative polymerase chain reaction following culture on the scaffolds of adipose-derived stem cells (ASCs) in osteogenic medium. As discussed below, other embodiments using different SMP compositions are also possible.

Figure 4:
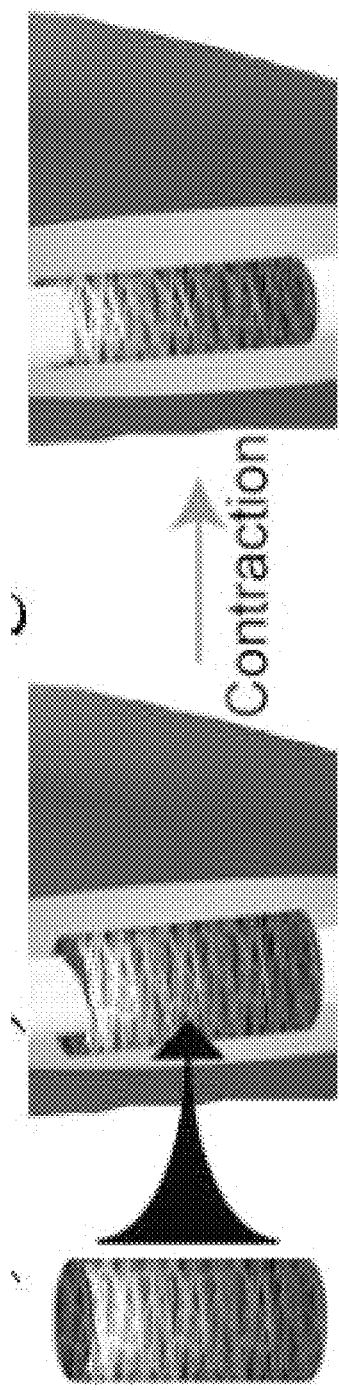
FIG. 4 is a schematic of a osteoconductive sleeve according to the present invention that can undergo programmed radial contraction to stabilize a defect site and promoting healing.
Figure 5:
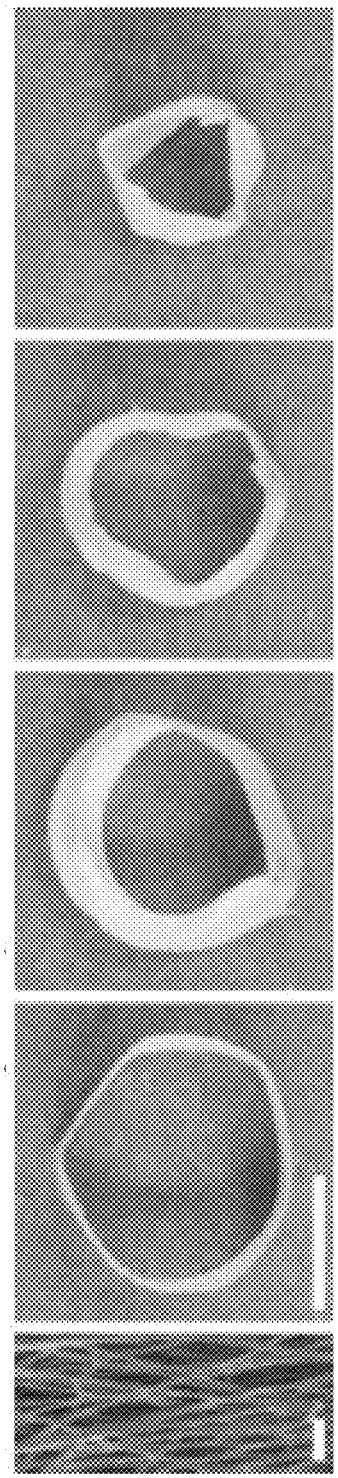
FIG. 5 is a series of images of a nanofibrous sleeve contracting during heating, where the scale bar is 10 μm is the first image and the scale bar is 500 μm in the remaining images.

The second component is an SMP sleeve 2 that can undergo programmed radial contraction under simulated physiological conditions. Referring to FIG. 4, the osteoconductive biomaterial sleeve employs SMP functionality to contract for the purpose of confirming to and stabilizing a defect site while concurrently promoting healing as a biomimetic periosteum and anchoring the sleeve to the intact neighboring bone, thereby simplifying surgical management of the injury. Use of a nanofibrous mesh can maximize osteoconduction, graft remodeling, and regeneration of a functional periosteum in situ. By providing a compressive barrier, the sleeve can also contain and stabilize autograft, allograft, or synthetic bone graft, including the first component described above. In a preferred embodiment, the second component comprises a thermoplastic polyurethane (TPU) with a biodegradable and glassy soft segment adapted to obtain an actuation temperature that can be tailored by adjusting the deformation temperature, slow degradation over weeks, and cell viability comparable to that of the untreated control. Alternatively, high molecular weight versions of the polyol (soft segment) itself—poly(D,L-lactide) may be used. Here, the molecular weight must be sufficiently high to allow for both electrospinning of nanofibers and also entanglement-based elasticity (achieved in the TPU by hard-block crystallization) required for shape contractions upon stimulation. As another alternative, poly(vinyl acetate) may be used. Nanofibrous sleeves may be prepared by electrospinning and engineered to contract in response to stimulation. The changes in shape of sleeves may be quantitatively characterized when fixed in a radially expanded state and actuated to contract by slight heating, hydration, and/or degradation, such as those seen in FIG. 5. Contraction and stabilization of a defect may be simulated and assessed by imaging recovery of scaffolds around a mock defect, for which two dowels can be used, with assessment of anchoring by pull-out tests. Osteoconductive capacity may be assessed as described above.

Figure 6:
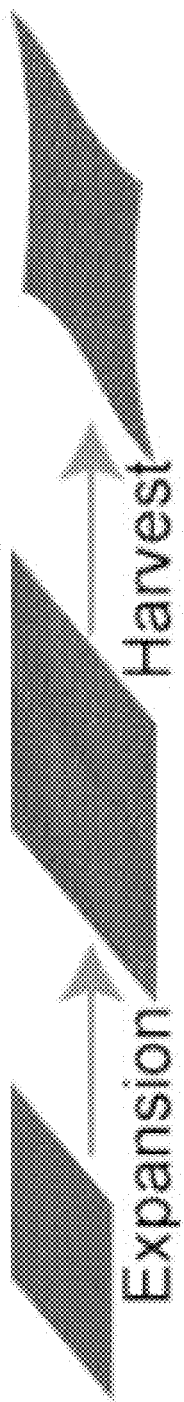
FIG. 6 is a schematic of a two-dimensional cell culture substrate according to the present invention that can undergo programmed expansion to provide biomimetic biomechanical stimulation to stem cells during engineering of periosteal sheets for use as periosteal grafts.

The third component is a two-dimensional cell culture substrate 3 that can undergo programmed expansion or topographic change for mechanobiological engineering of periosteal sheets in vitro. The two-dimensional SMP substrate employs shape-memory expansion to provide biomimetic biomechanical stimulation to stem cells during engineering of periosteal sheets in vitro. The substrates use a co-polymer system incorporating the monomers tert-butyl acrylate and butyl acrylate. Alternatively, the commercially available optical adhesive, NOA-63, and similar formulations may be used for this purpose, the sole requirement being that the polymer system be glassy, crosslinked, and feature a glass transition temperature tunable in the 30-50° C. range. As seen in FIG. 6, substrate expansion will provide attached stem cells with tensile stimulation that mimics that present during in vivo development. Control over the actuation temperature can be achieved by systematically varying the weight percentage of tBA and BA in the copolymer while keeping the crosslinking density constant. It is possible to quantitatively characterize gradient substrates that expand non-uniformly (when fixed following cantilever bending) when actuated by slight heating, as seen in FIG. 7. To determine optimal expansion magnitude and rate, ostogenic induction may be assessed on high-density cell sheets cultured on the gradient samples, using the assays described above. Both human ASCs and the multipotent mouse embryonic fibroblasts cell line C3H/10T1/2 may be assessed. Cell sheets will be harvested following culture using from the substratum using a cell scraper. Cell sheets will then be cultured on cell culture dishes and on flat samples of the sleeve according to the present invention and characterized for osteogenic and osteoconductive capacity, as described above.

As explained herein, various compositions that can serve as each component were prepared and tested to determine shape memory characteristics as well as to glean the particular cellular interactions necessary for the use of the present invention.

Example 1—SMP Scaffold

Foam scaffolds were fabricated using a modified porogen-leaching technique. A functionalized poly(ε-caprolactone) (PCL) macromer and a second functionalized hydrophilic macromer based on poly(ethylene glycol) (PEG) were mixed with salt in a 9:1 salt-to-polymer ratio and crosslinked via thiol-ene chemistry using a photoinitiator. After synthesis the salt particles were extracted using water, creating a porous foam scaffold with high porosity.

The ability of the foam scaffold to fill space was determined by characterizing its shape memory behavior using a dynamic mechanical analyzer (DMA). Circular discs were heated above their melting transition temperature, compressed, cooled to fix the temporary deformation, and then heated back above the melting temperature to expand to the original shape. The resulting fixing and recovery ratios were measured.

The ability to tune the recovery temperature to a physiological temperature was investigated via two methods. First, the ratio of the two macromers during synthesis was systematically varied and the resulting melt transition was determined using a differential scanning calorimeter (DSC) of the scaffolds in the dry and hydrated states. Second, the temperature at which the scaffolds were deformed during the shape memory process was varied and the resulting onset of recovery was measured using a DMA.

Pore architecture and interconnectivity was investigated using microtomography (μCT) and the shape memory effect on the porous structure was analyzed using scanning electron microscopy (SEM). Preliminary cell culture studies were performed to test the cytocompatibility of the scaffolds. Human adipose derived stem cells (hASCs) were seeded on the material and assayed using SEM and Live/Dead staining 2 d and 4 d after seeding.

Thermomechanical testing showed that the foam had excellent compressive shape memory properties: the shape fixing and recovery ratios of the material were 99 and 95%, respectively, as determined from the one-way shape memory cycle (data not shown). The foam also revealed a high compression ratio as it was able to be compressed to ~25% of its original thickness without failure and with recoverability.

Tuning of the transition temperature was achieved by varying the weight ratio of the two functionalized macromers during fabrication and varying the deformation temperature during the shape memory cycle. It was observed that, for samples hydrated to equilibrium, as the weight fraction of the hydrophilic macromer was increased the resulting melting transition temperature as measured from DSC decreased, with a range near body temperature. Also, as the deformation temperature decreased, the resulting onset of recovery decreased. However, decreasing the deformation temperature also led to a decrease in fixing ratio (data not shown).

Pore microstructure was observed using uCT analysis and it was found that scaffolds with porosities >80% and high interconnectivities were achieved (data not shown). SEM analysis of scaffolds prior to fixing, after fixing, and after recovery revealed that macroscopic compression led to microscopic compression of the pore structure. Gratifyingly, this microstructural transformation was subsequently restored upon recovery.

Cell culture experiments were conducted to test cytotoxicity of the scaffolds. SEM analysis after 2 d and 4 d revealed cells attached and were well spread in the scaffold (data not shown). Live/Dead analysis revealed cells remained viable after 2 d and 4 d and cells had proliferated on the scaffold (data not shown).

This embodiment of the present invention thus provides a cytocompatible scaffold capable of being fixed in a compressed state and recovering to expand to the original state at a physiological temperature. The scaffold showed excellent shape fixing and recovery in compression and the transition temperature was able to be tuned through composition variation and control of the deformation temperature.

Example 2—SMP Scaffold

Another embodiment of the present invention involves a crosslinked poly(caprolactone) (PCL) scaffold prepared using a porogen-leaching technique. A functionalized PCL macromer was mixed with salt in a 9:1 salt-to-PCL ratio and crosslinked with tetrathiol. After synthesis the salt particles were extracted using water, creating a porous foam scaffold with high porosity.

Following salt extraction, the melting temperature of the scaffold was determined using differential scanning calorimetry (DSC), and the shape memory properties characterized using dynamic mechanical analysis (DMA). Samples were heated above their melting temperature, uniaxially stretched, cooled to fix the temporary deformation, and then heated above their melting temperature to recover to the permanent shape. The resulting fixing ratio (how much of the deformed strain is maintained upon fixing) and recovery ratio (how much of the temporary strain can be recovered) were measured. Pore morphology was investigated using scanning electron microscopy (SEM) at each stage of the shape memory cycle.

Preliminary cell culture studies were performed to test material biocompatibility and attachment. For this study, C3H10T1/2 mouse fibroblasts were seeded on the scaffold material. A Live/Dead assay was performed to assess cell viability and penetration into the scaffold.

Thermomechanical testing showed that the foam had excellent shape memory properties: the shape fixing and recovery ratios of the material were 99 and 93%, respectively, as demonstrated by a one-way shape memory cycle for the PCL foam in tension. With high fixing and recovery percentages, this material is a good candidate for being manipulated to fill critical-sized defects, though requiring lowering of the transition temperature by composition alteration.

To determine pore microstructure, SEM was conducted on the top surface of the foam prior to fixing, after fixing, and after recovery, as seen in FIG. 8. As synthesized, the pore structure is round and open. After uniaxially stretching and fixing the pores become elongated. After recovery the pores return back to a more rounded morphology.

Cell culture experiments were conducted to test cell viability and penetration into the scaffold. More than 99% of the cells were viable and cells were seen at depths up to 120 as shown in FIG. 9. Here cells were seeded on a static scaffold that did not undergo any active shape change. Given the excellent viability and penetration of cells into the scaffold as well as the excellent shape fixing and recovery of the scaffold, shape recovery is anticipated to present cells with substantial biomechanical stimuli. It may be possible to tune such stimuli to control cell behavior.

This embodiment of the present invention provides a biocompatible scaffold with shape-changing capabilities. The SMP employed exhibited excellent shape fixing and recovery as well as control over pore morphology through the shape memory effect. Cells readily attached, penetrated and remained viable in the scaffold.

Example 3—SMP Scaffold

To prepare highly porous scaffolds using a robust and simple technique, a modified porogen-leaching process was employed, similar to a method established by Zhang and colleagues for PCL-block-Polydimethylsiloxane SMP foams. Functionalized PCL and PEG macromers were dissolved in dichloromethane (DCM) and combined with tetrathiol crosslinker and 2, 2-dimethoxy-2-phenylacetophenone photoinitiator as seen in FIG. 10. This solution was added to fused NaCl crystals in a 1:9 polymer:salt ratio by weight and UV cured. The fusion of salt particles, prior to the addition of the macromer solution, was performed to improve the pore interconnectivity. Following curing, salt was extracted in water, yielding highly interconnected porous foams with porosities of 79±5% as determined by microtomography. Volumetric shrinkage of scaffolds was observed following the first heating cycle and this shrinkage was dependent on the macromer concentration in DCM.

The shape memory behavior of the scaffold was quantitatively characterized using a one-way shape memory compression test. Prior to testing, samples were thermally treated by heating to 80° C. for 10 min followed by cooling to −4° C. for 10 min to remove residual stresses generated during curing. To test shape memory behavior, circular disks of the scaffold were heated to 80° C. and uniaxially compressed. While maintaining the compressive deformation, the samples were cooled to 0° C. to induce crystallization, immobilizing the chains and fixing the deformation. Upon unloading, a fixing ratio—how much of the programmed deformation is maintained upon unloading—of 99±0.5% was observed. Samples were then heated to 80° C. to trigger recovery of the scaffold, with a recovery ratio—how much of the programmed deformation is recovered upon heating—of 97%±1.4% observed. The programmed state remained stable at room temperature with no observable premature recovery during 6 d of storage. Stability of temporary shapes is a desirable characteristic both for tissue engineering scaffolds and for active cell mechanobiology studies, in which cell seeding is performed in the temporary state.

To determine the effect of shape memory on macroscopic and microscopic scaffold architecture, scanning electron microscopy (SEM) was performed. Prior to programming the temporary shape, SEM of the scaffold cross-section revealed an open pore structure with high interconnectivity. Upon programming the compressive deformation, the porous architecture collapsed as struts began layering on top of one another, significantly reducing the porosity. Importantly, the porous architecture was restored upon recovery of the scaffold, with no obvious compromise of the integrity of the internal foam walls, as observed visually from SEM or mechanically from repeated shape memory cycles where the material's modulus did not drop after three repeated cycles. Large compression ratios of up to 78% were achieved, which is desirable for tissue engineering strategies, such as minimally invasive delivery, or mechanobiological study of large tensile strains on cells seeded in fixed scaffolds. For example, in adult cardiac fibroblasts it has been shown that a 10% uniaxial tensile strain can stimulate extracellular matrix mRNA levels and transforming growth factor-β (TGF-β), whereas a 20% strain decreases extracellular matrix mRNA expression while stimulating TGF-β to a lesser extent. Ultralow porosity in the fixed state may inhibit cell infiltration into the scaffold when seeding in the temporary state. As a result, tissue engineering applications or cell mechanobiology studies for which large strain triggering is desired would be expected to have to balance the desired level of strain with the ability to achieve cell seeding in the fixed, low porosity state. Therefore, to enable studies on increasing levels of strain recovery, increasing porosity in the permanent state will be required. SMP scaffolds fabricated via the alternative method of gas foaming have been developed with permanent porosities of 98%, but with gas foaming pore interconnectivity is typically low, which would limit cell infiltration into such scaffolds. For the salt leaching approach employed in the present work, pore size, porosity and interconnectivity can be tuned through controlling the size of the salt particles, the degree of salt fusion, and the concentration of macromer in solvent. Control over the porous structure is important for cell mechanobiology studies, as previous studies on static scaffolds have shown that cell behavior is dependent on pore morphology and size.

Shape-changing scaffolds that can change shape under cell compatible conditions, particularly at or near body temperature, require control over the triggering mechanism. Shape recovery of semi-crystalline SMPs occurs at their melting transition temperature ($T_m$), and the $T_m$ of PCL is ~60° C., which is much higher than body temperature. Therefore, lowering of $T_m$ is necessary to fabricate a shape-changing PCL-based construct. Here, lowering of Tm was achieved via two mechanisms. The first mechanism utilized copolymerization of macromoners of PCL with PEG, a hydrophilic polymer. A PCL-PEG hydrogel with a $T_m$ of 31° C., where tuning of the Tm was achieved through control over the molecular weight of the PCL18, has been reported. Here, the molecular weight of the macromers were kept constant and the weight ratios of each varied to control the $T_m$.

Differential scanning calorimetry revealed that the $T_m$ of the scaffold in both the dry and wet states decreased with increasing PEG content. As a consequence of increasing PEG, the water uptake of foams also increased. Employing this design strategy, a range of $T_m$'s around body temperature was achieved, with a composition of 80 wt-% PCL and 20 wt-% PEG yielding a hydrated $T_m$ of 37° C.

In addition to copolymerizing the PCL scaffolds with PEG for melting point modulation, the programming temperature of the SMP foam was also varied to lower the apparent $T_m$, or onset temperature for shape recovery. Scaffolds were heated to different temperatures ranging from 30° C. to 80° C. then uniaxially compressed. After reaching either a predetermined strain of 30% or the force limit of the tensile testing device, the scaffolds were next cooled to 0° C. to fix the deformation by crystallization. It was observed that for deformations well above $T_m$ of the construct, there was little dependence of onset temperature for recovery on deformation temperature. However, as the deformation temperature approached $T_m$ from above, an associated decrease in the onset temperature was observed. Such a "temperature memory" phenomenon was previously reported where a large alpha transition related to the ionic cluster phase is largely responsible for this effect. A related phenomenon has been exploited in amorphous systems to tune the recovery temperature and recovery kinetics, where deforming at or below the glass transition temperature led to lower recovery temperatures. This phenomenon has also been observed in semi-crystalline polymers where recovery temperatures spanning a range of 100° C. were achieved. The present invention is the first instance of semi-crystalline SMP foams exhibiting such temperature memory.

Although deforming near $T_m$ results in a lowering of the onset temperature for strain recovery to within a physiological range, an unintended consequence of this approach is a reduction in the stability of the temporary shape at room temperature, examined by dwelling at that temperature during the heating step of the shape memory cycle, along with a reduction in fixing ratio. As the deformation temperature decreased, a corresponding decrease in stability was observed. The reduction in fixed strain stability at room temperature may be attributed to relaxation of internal stresses between the high melting fraction of the material, which is elastically deformed at the lower temperature and thus under compressive stress, and the lower melting fraction, which is otherwise well fixed put into tensile stress by the high-melting fraction. Despite these complexities, the temperature memory effect offers a useful tool to control the recovery temperature of this SMP foam.

Surprisingly, the foams according to the present invention also exhibited two-way reversible shape memory under the bias of a compressive load, consisting of dramatic cooling-induced compression and heating-induced expansion. By inspection, neither effect is due to ordinary thermal expansion effects; rather, crystallization of the foams under a compressive load results in additional contraction that is reversed upon heating through $T_m$, with thermal hysteresis of ca. 50° C. for the heating rate used. This effect is repeatable through several cool-heat cycles and represents a new example of reversible, soft actuation. For these samples, a compressive actuation strain of ca. 15% was achieved through contraction upon crystallization. Interesting, this actuation strain is non-monotonic in the initial strain applied, indicating competing effects of strain that drives crystallization-induced actuation, and an upper bound of compressive strain for the foams. This is the first instance of an SMP scaffold with two-way reversible shape memory in compression. Two-way reversible actuation has been studied in other material systems, such as shape memory alloys, for application in reversible actuators. Incorporating this functionality in a cytocompatible scaffold creates the possibility for generating cyclic loading on attached cells by simply switching the incubation temperature.

Example 4—SMP Scaffold

SMP scaffolds were fabricated using a modified porogen leaching technique, in which a functionalized poly(ε-caprolactone) (PCL) macromer was mixed with NaCl in a 9:1 salt-to-PCL ratio by weight and subsequently crosslinked via thiol-ene chemistry. Salt particles were fused for 24 h in a humidity chamber prior to adding the macromer solution. Once the polymer was cured, salt particles were extracted with water, yielding a porous foam scaffold with high porosity and interconnectivity. Shape memory characterization of the scaffold was performed using a dynamic mechanical analyzer measuring compressive strain fixing and recovery. The resulting porous architecture before fixing, after fixing, and after recovery was investigated with scanning electron microscopy (SEM) and microtomography. Tuning of the functional recovery temperature to a cytocompatible temperature was achieved through both composition and deformation temperature adjustments. Cell studies were performed using human adipose derived stem cells to investigate cell viability and cell proliferation on the scaffolds.

The porogen-leaching technique yielded polymeric scaffolds featuring porosities >80% with high interconnectivity. These scaffolds exhibited excellent shape fixing and shape recovery characteristics, with fixing and recovery ratios of 99% and 95%, respectively. Prior to deformation and fixing, pores were open and interconnected, whereas after compressive deformation pore architecture collapsed; pore structure was able to then recover to the original size and shape after recovery, as seen in FIG. 11. The functional recovery of the scaffolds was easily tuned by adding a second functionalized macromer to the system. This hydrophilic macromer, once hydrated, served to decrease the recovery temperature to 37° C. Deformation temperature also served as a viable method for controlling the recovery temperature, with lower deformation temperatures leading to lower recovery temperatures. Preliminary cell studies using Live/Dead viability assay revealed cells attached and remained viable after 4 d on the scaffold (data not shown). SEM imaging of cells seeded on the scaffold revealed cells proliferated to cover the surface of the scaffold and cells appeared well spread on the scaffold (data not shown).

Example 5—SMP Scaffold

An SMP scaffold was formed using the aforementioned modified porogen leaching technique, in which tert-butyl acrylate (tBA), butyl acrylate (BA), tetraethylene dimethacrylate (TEGDMA) as a crosslinker, and 2,2-Dimethoxy-2-phenylacetophenone (DMPA) as a photoinitiator were mixed in a template of fused NaCl and crosslinked via UV-initiated free radical polymerization. To fabricate a foam with a hydrated Tg of 37° C., a solution of 92 wt-% tBA and 8 wt-% BA was mixed with TEGDMA (5 wt-% relative to the amount of tBA and BA) and DMPA (1 wt-% relative to the amount of tBA and BA) and added to the salt template. The solution was then cured in a UV box for 2 h followed by drying in a vacuum oven for 24 h. After drying, salt particles are extracted in 50° C. (temperature above Tg) water for 48 h. As seen in FIG. 12, thermogravimetric analysis of 92tBA-8BA foams reveals than when heating to 600° C. no salt remains, as the final weight of 6% is the same as for the films of the same compositions. Samples were heated at 10° C./min to 600° C. The Tg-based foam has a stiffness an order of magnitude higher than the semi-crystalline based system. As seen in FIGS. 13A and 13B, the storage modulus sweep for 92tBA-8BA foams (FIG. 13A) show a storage modulus an order of magnitude higher than the 80PCL-20PEG foams (FIG. 13B) when dry. Note that due to the large stiffness of the tBA/BA foam, the storage modulus drop could not be measured in the DMA with the given parameters (data ends right as modulus drop begins at 60° C.).

Example 6—SMP Scaffold

In another embodiment of an SMP scaffold seen in FIGS. 14 and 15, a PDLLA diol may be end-capped with an acrylate endgroup, following a protocol established by Y. Zhang, C. Y. Won and C. C. Chu, *Journal of Polymer Science Part A: Polymer Chemistry,* 1999, 37, 4554-4569, hereby incorporated by reference in its entirety. Briefly, a PDLLA diol may be dissolved in anhydrous THF in an ice-chilled flask under nitrogen. Triethylamine in a molar ratio of 4:1 (triethylamine:PDLLA diol) may be added to the reaction flask, followed by an equimolar amount of acryloyl chloride (relative to triethylamine). The reaction may be carried out for 3 h at 0° C. followed by 18 h at room temperature. This is expected to yield the highest degree of end-capping according to Zhang. Endcapping of a PDLLA diol having a MW of 10.4 kDa with acryloyl chloride following this procedure resulted in incomplete functionalization and, as a result, the foam was not fully cross-linked. Moisture may have inhibited the reaction as this system is moisture sensitive so formation of this embodiment may require a high degree of moisture control.

Example 7—SMP Scaffold

In this embodiment, the scaffold comprises a polyurethane-based shape memory foam where PDLLA is be used as the soft block and POSS is used as the hard block. The chemistry is the same as that employed for the contracting sleeve below. To achieve a foam, TPUs with differing molecular weights may be dissolved in chloroform and vacuum infiltrated into a fused salt template. After infiltrating into the template, the chloroform may be removed from the system in a vacuum oven. To fix in the permanent shape of the foam, samples may be heated to 130° C. for 10 min to melt the POSS domains. The foams may then be cooled to room temperature to allow recrystallization of POSS, setting the permanent shape and removing any residual stress in the material.

Following thermal removal, salt may be extracted from the foams for 24 h in water at 50° C. (a temperature above Tg of the TPU). Foams may then be dried and the thermal, thermomechanical, shape memory, and degradation properties will be characterized. A foam fabricated using a TPU with a molecular weight of 34 kDa was made by first dissolving the TPU in chloroform in a 50% (w/v) concentration, and the vacuum infiltrating into a template. Salt was completely extracted as shown in the TGA trace. As seen in FIGS. 16 and 17, thermal characterization revealed a dry Tg of 48.9° C., which is expected to decrease ~10° C. upon hydration, as observed in studies on the contracting sleeve. Foams with Mn=~60 kDa and ~160 kDa may be formulated to investigate the effect of molecular weight on thermal, thermo-mechanical, shape memory, and degradation behavior.

Example 8—SMP Sleeve

Electrospun scaffold meshes were prepared from a custom synthesized shape-memory thermoplastic polyurethane and employed as programmable scaffolds as follows: a dynamic mechanical analyzer was used to uniaxially stretch scaffolds to 100% strain at 65° C. (above Tg, glass transition temperature) and fixed at 0° C. in an elongated state. Human adipose-derived stem cells (ASCs) were cultured on either the temporarily aligned scaffolds or the previously recovered scaffolds (as a random control) at 30° C. for 24 h. Shape change was triggered by increasing the temperature to 37° C. Cells were cultured at 37° C. for an additional 24 h.

Scaffold architecture and cell orientation and morphology were assayed before and after shape transition by scanning electron microscopy (SEM) and fluorescence imaging. Two-dimensional fast Fourier transform (2D FFT) analysis was used to characterize the alignment of actin filaments with the corresponding scaffold structure change. The degree of actin filament alignment was determined by the amplitude and shape of the peaks in each FFT plot. The higher the peak, the more precisely the actin filaments were aligned along a principle direction.

The programmable shape-changing electrospun scaffold retained an aligned structure when held at 30° C. (below Tg). The scaffold underwent substantial fiber reorientation and pore size alteration during the heat-triggered shape change. The structure change of the programmable shape-changing scaffold directed cell morphology and orientation compared to the static random control. For cells cultured on a temporarily aligned fibrous scaffold, there are two distinct peaks, at 90° and 270°, in the FFT plot compared to cells cultured on the previously recovered random fibrous scaffold. After activating shape change, cells lost their preferential alignment corresponding to fibrous structure change; no prominent peak was generated in the FFT plot. Fluorescent imaging further showed cytoskeletal filaments reorganization after the temporarily aligned fibrous structure recovered back to its permanent random structure. Cells remained randomly orientated on the previously recovered fibrous scaffold.

Example 9—SMP Sleeve

Electrospun scaffolds for use as the second component of the present invention were fabricated from a custom-synthesized shape-memory thermoplastic polyurethane and employed as shape-changing scaffolds as follows. An electrospun scaffold with randomly oriented fiber architecture was uniaxially stretched in a dynamic mechanical analyzer to 100% strain at 60° C. (above Tg, glass transition temperature) and fixed at 0° C. in the temporarily elongated shape, which exhibited a strain-aligned fiber architecture. Human adipose-derived stem cells (hASCs) were seeded on the strain-aligned (active) scaffolds as well as on unaligned and aligned control (static) scaffolds, and cultured at 30° C. for 24 h. The temperature was then increased to 37° C., triggering a change from aligned to unaligned fibers in the active group, while the controls remained unchanged. Cells were then cultured at 37° C. for an additional 24 h.

Cell body alignment was assayed by fluorescence imaging before and after thermal triggering. Cells were labeled with Phalloidin to visualize filamentous actin. Two-dimensional fast Fourier transform (2D FFT) image analysis was used to characterize cell body alignment. The degree of cell body alignment was determined by the amplitude of peaks in each FFT plot, with higher peaks corresponding to higher alignment in a principle direction.

Viable cells remained attached on both active and static scaffolds before and after thermal triggering (data not shown). Shape-memory activated change in fiber alignment of the active scaffold altered cell body alignment, with no comparable change observed in the static controls. Before transition, cells cultured on the aligned fibers of the active scaffold demonstrated two distinct peaks in the FFT plot at 90° and 270°. After transition, cells lost their preferential alignment, with no prominent peaks in the plot and corresponding reorganization of cytoskeletal filaments was observed. In contrast, on the static unaligned and aligned controls cells remained randomly oriented or aligned, respectively, both before and after temperature change.

Example 10—SMP Sleeve

An SMP for use as the second component of the present invention may comprise a thermoplastic polyurethane (TPU) previously developed for use as a biodegradable stent coating. The polyhedral oligomeric silsequioxane (POSS) TPU features alternating hard segments of POSS and biodegradable, amorphous soft segments of polylactide/caprolactone copolymer (P(DLLA-co-CL)). To meet the specific requirements of the present invention, the material chemical composition was modified as follows. A polymeric diol chain was polymerized solely from lactide (LA) monomer, instead of synthesizing from the mixture of LA monomer and another biocompatible ester, ε-caprolactone (CL). CL was eliminated from the chemistry because a TPU synthesized from a LA/CL-based copolymeric diol has an undesirably low glass transition temperature (Tg) that leads to shape recovery at a temperature substantially lower than normal body temperature. The synthesis was carried out in a two-step process (Briefly, a polymeric diol of poly-DL-lactic acid (PDLLA) (hereafter called polyol) was synthesized by ring-opening polymerization of cyclic lactide monomer (3,6-dimethyl-1,4-dioxane-2,5-dione) in the presence of a prescribed concentration of initiating 1,4-butandiol and a small amount of organometallic catalyst. The polyol was then reacted with hexamethylene diisocyanate (HDI) and POSS diol (AL0130, Hybrid Plastics, Hattiesburg, Miss.), also in the presence of a small amount of organometallic catalyst. The targeted final molar ratio of polyol and POSS diol was kept at 1:3. The glass transition temperatures of the resultant TPU synthesis batches were in the range of ~48-49° C. All chemicals were purchased from Sigma-Aldrich (St. Louis, Mo.) unless otherwise noted.

To prepare structures that would allow changes of bulk shape as well as internal fibrous architecture in response to shape-memory actuation, scaffolds were fabricated using electrospinning. The detailed electrospinning apparatus setup was described elsewhere. The custom-synthesized TPU was dissolved in dimethylformamide (DMF; Sigma- Aldrich) and chloroform (Fisher Scientific, Pittsburgh, Pa.) at DMF:chloroform=1:2 (v/v). To ensure that the resultant electrospun fibers had similar diameters, the concentrations of polymeric solutions were adjusted between different TPU synthesis batches to accommodate variation in molecular weight, with the range of polymeric solution concentrations varied from 35%-45% (w/v). The polymeric solution was loaded in a syringe with a 22 G stainless steel blunt needle used as a spinneret. The polymeric solution was pumped at a rate of 0.4 ml/h through the spinneret, which was positively charged to 15.5 kV. The rotating drum was negatively charged to 0.5 kV with a 10 cm distance from the spinneret to rotating drum surface. The total duration of the electrospinning process was 12 h, yielding an electrospun scaffold of 100 µm thickness.

To produce static control scaffolds that do not change shape or fibrous architecture when heated to body temperature, scaffolds of either randomly oriented fibers or aligned fibers were prepared. To produce a randomly oriented scaffold, the rotation speed of the collecting drum was set at 400 rpm. The slowly rotating drum had a negligible effect on fiber orientation in these static unaligned control scaffolds. To produce an aligned scaffold, the rotation speed of the collecting drum was increased to 4000 rpm. The high-speed rotating drum preferentially oriented fibers along its circumferential direction in these static aligned control scaffolds.

The electrospinning process is known to stretch amorphous polymer chains. If the electrospun scaffold is subsequently heated to near or above the polymer glass transition temperature, the extended amorphous chains relax and release molecular-level strain, which subsequently causes dimensional changes in the electrospun scaffold. In the present invention, this premature shrinkage posed the risk of obscuring the subsequent programmed and desired shape memory effect. To remove molecular-level strain and to prevent premature shrinkage, a novel thermal treatment was used in which, all scaffold groups were immersed in a ~55-60 wt % Pluronic F127 thermoreversible hydrogel aqueous solution and heated and held isothermally at 70° C. (at which temperature the Pluronic solution is a gel) for 3 h to release the molecular-level strain while the hydrogel stabilized the fibrous architectures and prevented change in scaffold shape or fiber alignment. After thermal treatment, the scaffolds were rigorously washed in deionized water at 4° C. (at which temperature the Pluronic solution is a liquid) to remove the hydrogel and were then dried in a vacuum oven at room temperature.

To program the experimental active scaffold that can be triggered to change shape on command, a thermally treated randomly oriented scaffold was uniaxially stretched to 100% strain (during which the scaffold demonstrated contraction in the orthogonal plane with a Poisson's ratio of approximately 0.43) at 60° C. in a dynamic mechanical analyzer (DMA; TA Instruments Q800) and fixed in that temporary shape by cooling below Tg to 0° C. Active strain-aligned scaffolds prepared in this manner can be triggered to recover from their temporarily elongated shape with aligned fiber orientation to a more compact shape with random fiber orientation by heating to 37° C. under a hydrated condition.

Scaffolds were analyzed to characterize shape memory functionality, fiber architecture and size, and macroscopic shape change under simulated cell culture conditions. Shape memory functionality was analyzed using a one-way shape-memory cycle. Fiber architecture and size were analyzed by scanning electron microscopy (SEM) and two-dimensional fast Fourier transform (2D FFT) image analysis (n=3 micrographs from one sample of each group; all from TPU synthesis batch 2. Macroscopic shape change under simulated cell culture conditions was measured using digital calipers.

Human adipose-derived stem cells (hASCs) were used to investigate the effect of scaffold shape and architecture change on cell attachment, viability, and morphology. This cell type was selected because ASCs and other adult (or tissue) stem cells have previously been shown to demonstrate architecture-responsive behavior on porous 3D scaffolds, including electrospun scaffolds, and because ASCs are widely used in tissue engineering and regenerative medicine research and, therefore, would be likely candidates for use in future strategies employing SMP scaffolds. Prior to active cell culture experiments (experiments in which the scaffold was triggered to change shape and fiber architecture during culture), hASCs (Cat# R7788-115) were expanded in complete growth medium: MesenPro RS basal medium with 2% MesenPro RS growth supplement, 1% GlutaMAX, and 1% penicillin/streptomycin in a 37° C. humidified incubator with 5% $CO_2$. Cells were cultured on a T175 flask with 30 ml of complete growth medium. The medium was changed every four days and cells were passaged at 80% confluence using TrypLE Express solution. Cells were used at passage 6. All cell culture products were purchased from Gibco, Life Technologies (Grand Island, N.Y.).

Here, active cell culture is a two-stage process. During the first stage, cells are seeded and cultured on the active or static scaffolds at a cytocompatible temperature (30° C.) below body temperature, at which temperature the active scaffolds maintain their fiber alignment with little change in the macroscopic shape (length) of the scaffold. During the second stage, shape memory actuation is triggered by heating to body temperature (37° C.), resulting in changes in scaffold shape and architecture in the active scaffolds, while static control scaffolds remain unchanged. To determine whether changes in scaffold shape and architecture would affect cell behavior, hASC cytoskeletal and nuclear alignment were characterized before and after temperature transition during active cell culture experiments employing active and static scaffolds.

Active strain-aligned, static unaligned control, and static aligned control scaffolds were sterilized in a biological safety cabinet under UV light for 1 h each side and then hydrated in complete growth medium at room temperature for 20 min before seeding cells on the scaffolds. Scaffolds were then placed in 24-well plates and a droplet of cell suspension was laid on each scaffold with a cell density corresponding to 8,000 cells/$cm^2$ for the total scaffold area. Droplet coverage, which was highly reproducible between samples, was marginally less than the total scaffold area, producing a final cell seeding density greater than 8,000 cells/$cm^2$ (all downstream imaging analyses were performed on representative areas within the seeded region). The plates were incubated in a 30° C. incubator for 5 h to allow cell to attach on the scaffolds, and then an extra 500 µl of complete growth medium was added into each well. Two time points were selected to assay cell viability and morphology: during the first stage of active cell culture, cells were assayed after being cultured at 30° C. for 24 h; during the second stage of active cell culture, which was triggered by moving scaffolds to a 37° C. incubator, cells were assayed after being cultured for an additional 24 h. Scaffolds were fabricated from four TPU synthesis batches. Four scaffolds from each of the four synthesis batches were used for the three groups—active strain-aligned, static unaligned control, and static aligned control—providing a sample size of 16 (n=16) for each group at each time point.

To characterize cell cytoskeletal alignment and cell nuclear alignment, cytoskeletal actin filaments and cell nuclei were visualized by staining with Alexa Fluor 647 Phalloidin and SYTOX Green Nucleic Acid (Molecular Probes, Life Technologies), respectively. Samples were fixed, permeabilized, and stained following the manufacturer's instructions for phalloidin staining. Phalloidin was used at the concentration suggested in the instructions and mixed with a 1:6000 dilution of SYTOX green stain in phosphate buffered saline. Samples were mounted in ProLong Gold reagent for fluorescence imaging.

Cell imaging was performed using two forms of fluorescence microscopy for distinct purposes. To quantify cell cytoskeleton and cell nuclear alignment, LIVE/DEAD and phalloidin/SYTOX green stained cells were imaged on a Leica DMI 4000B inverted microscope outfitted with a Leica DFC 340FX camera and using a 10×/0.22 NA objective. To acquire higher resolution micrographs suitable for qualitative analysis of cell morphology and quantitative analysis of cell distribution, phalloidin/SYTOX green stained cells were imaged on a Zeiss LSM 710 confocal laser-scanning microscope (CLSM) using a 40×/1.30 NA oil objective with Zeiss immersol 518 F immersion oil. Red or green pseudocolor was applied using ImageJ, with a lookup table applied to all micrographs. Histogram stretching was applied to phalloidin/SYTOX green images in order to maximize printed image contrast.

To quantify cell cytoskeleton alignment on the active and static scaffolds, a 2D FFT image analysis method was adopted and used [32]. Images of cells stained with phalloidin were characterized to determine the extent to which cell cytoskeleton alignment was controlled by scaffold architecture. A 1600×1200 px image was cropped to a square of 1024×1024 px and then overlaid with a black square mask with a concentric transparent circle (1024 px in diameter) to avoid edge/corner effects. The masked image was computed using the FFT function in ImageJ. Pixel intensity along each radius (from 0° to 359° with 1° increment) in the FFT plot was summed using the ImageJ plugin "Oval Profile." Pixel intensities of the 16 images were summed. The pixel intensity of each radius was normalized by the minimum intensity value. Subsequently, the baseline was shifted to 0 by subtracting 1 from each value. The sample size for analysis of cell cytoskeleton alignment was 16 (n=16). Pixel intensity was plotted with a range from 0 to 0.15.

To allow comparison of cell nuclear alignment on the active and static scaffolds, a previously reported method was adapted to quantify the degree of nuclear alignment. Briefly, the nuclear angle of each cell was measured using ImageJ, and the standard deviation of nuclear angle distribution was determined. The standard deviation was used to quantify the degree of cell nuclear alignment. Randomly oriented nuclear angles would produce a standard deviation of 52°, while perfectly aligned nuclear angles would produce a standard deviation of 0°. Because a standard deviation of 0° is statistically improbable for a cellular system of this nature, in the present work the standard deviation of nuclear angle distribution observed on the unaligned control and recovered-to-random samples and on the aligned control and strain-aligned samples were used to define the effective range of standard deviations for unaligned and aligned cells, respectively, in this system. The sample size for statistical analysis of cell nuclear alignment was 16 (n=16).

Cell viability was qualitatively determined using LIVE/DEAD reagents (Molecular Probes, Life Technologies). LIVE/DEAD was used at a concentration of 2 μM for both Calcein AM and Ethidium homodimer-1. Samples were stained following the manufacturer's instructions with a 30 min incubation at room temperature. The sample size for analysis of cell viability was 16 (n=16). Because cell viability in these samples was qualitatively observed to be high in all groups 24 h before and 24 h after temperature transition, a subsequent quantitative analysis of cell viability out to 72 h following change in scaffold shape and architecture was performed; samples from synthesis batch 4; n=2-3 samples per group). Cell distribution within the scaffold both before and after shape memory actuation was determined by confocal fluorescence microscopy of one set of representative samples from each of the strain-aligned and recovered-to-random groups in which cells were stained by phalloidin and SYTOX green.

The 95% confidence interval of the standard deviation of cell nuclear angle distribution was calculated using a bootstrap method. Permutation-based one factor ANOVA was performed to test for significant differences between the standard deviation of cell nuclear angle distributions among the three groups (strain-aligned, unaligned control, and aligned control) followed by multiple comparisons. Statistical significance was determined at p<0.05. The sample size for statistical analysis of cell nuclear alignment was 16 (n=16).

The electrospun scaffold demonstrated desirable shape memory functionality, in terms of shape fixing and shape recovery. A one-way shape-memory cycle showed that the scaffold had a high shape fixing ratio of 99%, meaning that the programmed scaffold can retain 99% of the deformation strain after the applied load is removed. The cycle also showed that the scaffold had a high shape recovery ratio of 95%, meaning that the scaffold recovered 95% of the deformation after shape-memory actuation.

Scanning electron microscopy revealed changes in the architecture of the shape-changing strain-aligned scaffold following thermal triggering. After the programmed uniaxial stretching, the strain-aligned scaffold showed prevailing fiber alignment. After incubation at 30° C. for 24 h and before shape memory actuation, the scaffold retained its temporarily aligned fibrous architecture and showed only modest change in macroscopic shape. After shape memory actuation by heating to 37° C., the scaffold recovered back to a randomly oriented architecture within 24 h and returned to within 20% of its original macroscopic length.

Strain-aligned and aligned control scaffolds both demonstrated a prevailing fiber alignment, as demonstrated by two distinct peaks at 90° and 270° in the FFT plots. Conversely, recovered-to-random and unaligned control scaffolds had no apparent fiber alignment, as demonstrated by a lack of distinct peaks in the FFT plots. In contrast to the difference in fiber alignment observed before and after shape memory actuation, the fiber diameter of strain-aligned and recovered-to-random scaffolds was not significantly different (p=0.29, by permutation testing).

A triggered change in scaffold architecture had a significant effect on cell cytoskeleton orientation. A change in scaffold fiber alignment via shape memory actuation was found to cause cells to change from preferential alignment of actin filaments along the fiber direction to a more random orientation. Before triggering scaffold architecture change, two distinct peaks at 90° and 270° in the FFT plot indicated that actin filaments were aligned along a principle direction, which was the scaffold fiber direction. After transition, actin filaments lost their preferential alignment, as indicated by a lack of distinct peaks in the FFT plot. Control groups that did not change scaffold architecture confirmed that cell cytoskeleton reorientation was induced by a change in scaffold fiber alignment rather than by the temperature transition. The FFT plots showed a lack of distinct peaks for the unaligned control and two distinct peaks for the aligned control, both before and after temperature transition. Although FFT peak height is not an accurate indicator of alignment—with width at half height being instead a more accurate measure of alignment—the shape of the FFT plot for the aligned controls before and after temperature change does suggest that the cytoskeletal organization changed subtly between the first time point (at 30° C.) and the second time point 24 h later (at 37° C.). Whether the subtle changes in cytoskeletal organization on these control scaffolds is due to changes in cell behavior over time, to the change in temperature, or to a combination of the two remains to be determined. Regardless, the controls confirmed that cell cytoskeleton reorientation on the experimental, architecture-changing groups was induced by a change in scaffold fiber alignment rather than simply by the temperature transition.

A triggered change in scaffold architecture also had a significant effect on cell nuclear alignment. Angular histograms showed a narrow distribution of cell nuclear angles on active strain-aligned and aligned control scaffolds and a broad distribution of cell nuclear angles on recovered-to-random and unaligned control scaffolds. Before triggering of scaffold architecture change, cell nuclei preferentially aligned in the direction of scaffold fiber direction with a standard deviation of cell nuclear angle distribution of 41.87±3.21°. After triggering a change in scaffold fiber alignment, cell nuclei became more randomly oriented with a standard deviation of cell nuclear angle distribution of 47.43±1.71° (p=0.001). Cell nuclear alignment remained unchanged for the two static control groups. Before and after shape memory actuation, the standard deviation of nuclear angle distribution for unaligned) (~46-47° and aligned)(~35-37° control scaffolds respectively defined the effective range of standard deviations for unaligned and aligned cells in this system.

Qualitatively, LIVE/DEAD assay showed cells were viable in all groups before and after temperature transition. Cells that were seeded on the active strain-aligned scaffold remained viable and attached after shape-memory-actuated scaffold fiber alignment change. Quantitative analysis of cell viability out to 72 h following change in scaffold shape and architecture showed that cell viability remained greater than 86% for all groups at all time points. Although this study was not designed to reveal the limit of tolerable deformation, or, in fact, ranges of cellular responses to different deformation levels, cells were found to remain attached and viable even when the strain-aligned scaffold was fixed at 200% strain (rather than the 100% strain used throughout this study). Confocal fluorescence microscopy showed that cells infiltrated 21 µm or more (two to three cell depths) into the scaffold during the first 24 h of culture at 30° C., at which point shape-memory recovery was triggered. After culture for an additional 24 h at 37° C. during and following scaffold shape-change, cells had infiltrated 42 µm or more (four to six cell depths) into the 100 µm thick scaffold.

Example 11—SMP Sleeve

Preliminary in vivo results in a mouse femoral segmental defect model have demonstrated that the TPU sleeve of the present invention may tear at the bone-graft junctions. One approach to reinforcing the TPU sleeve is to incorporate a semi-crystalline polyester, poly(L-lactic acid) or PLLA, during sleeve fabrication via a co-electrospinning process. PLLA fibers may be blended with TPU fibers at 20% volume ratio (controlled by varying solution feeding rate) throughout the entire thickness of the sleeve. The stability provided by the PLLA-TPU sleeve will be assessed by torsional and four-point bending mechanical tests. Another approach is to add a mesh of suture to the center of the tube to provide additional mechanical rigidity and tear resistance. Sutures are laid across the material at a specified pitch in both a clockwise and counterclockwise direction. This reinforcement will provide increased mechanical rigidity and tear strength, while not reducing the beneficial porosity of the material.

Example 12—Cell Culture Substrate

In this example, a co-polymer system with tert-butyl acrylate (tBA) and butyl acrylate (BA) was used for producing substrates capable of programmed topography transition suitable for controlling cell morphology with the intent of lineage specification for periosteogenic cell culture and tissue engineering Specifically, a buckling phenomena upon contraction of a thin, rigid material atop a thick, compliant layer was used to produce nanoscale wrinkles whose dimensional properties depend on the amount of contraction and thickness and stiffness of each layer. The film was cured with a transition temperature near 45° C. dry, which lowered when plasticized by water. This 1 mm thick film was then cut to 6 mm×24 mm and stretched to 12% uniaxial tensile strain in a DMA. This strain was fixed by holding the strain and cooling to 10° C. The programmed substrate was then placed into a gold sputter coater and sputter coated for 100 s to produce a thin, rigid layer atop the SMP film. Human adipose derived stem cells were plated on this substrate and cultured at 30° C. for 5 h. Topography change was found to control stem cell morphology, as intended. Cell nuclear and filamentous actin staining of human adipose derived stem cells plated on the temporarily flat substrate was randomly oriented. Following move of the substrate to a 37° C. incubator and cultured for 24 h, which results in the topographic trigger to the wrinkled topographic surface, the stem cells became preferentially oriented.

Example 13—Cell Culture Substrate

Using a co-polymer system with tert-butyl acrylate (tBA) and butyl acrylate (BA), the effect of cell seeding density on both the expanding substrates and topography changing (wrinkling) SMP substrates was studied. Both multipotent C3H10T1/2 mouse embryonic fibroblasts and multipotent human adipose derived stem cells (hASCs) were studied, as these two multipotent cell types both have the potential for use in an in vivo mouse model. Briefly, cells were seeded at either $10^5$ or $2 \times 10^5$ cells per ml on the gradient expanding or topography changing (wrinkling) substrates and cultured at 30° C. to confluence, at which time the substrates were triggered to change shape by warming to body temperature (37° C.). Cell morphology and behavior were analyzed qualitatively by light microscopy at 1, 3, 4, 5, 6, 7, and 8 days of culture.

Both cell types attached to and proliferated on the expanding and topography changing (wrinkling) substrates. hASCs showed apparent weaker attachment to the substrate, with cells tending to form nodules and cell sheets delaminating over time, and reduced proliferation compared to the C3H10T1/2 cells.

To determine whether improved cell attachment would improve hASC proliferation and spreading, hASCs were subsequently seeded on gelatin coated samples at densities of $2 \times 10^5$ or $3.3 \times 10^5$ cells per ml. The improved cell attachment provided by the gelatin coating was found to result in more uniform cell attachment, spreading, and proliferation, indicating that the substrates are suitable for use with hASCs, given appropriate surface modification to enable robust attachment.

Cell viability and adhesion on bare (unmodified) substrates were found to be suitable and gelatin coating significantly improved the attachment of hASCs. hASCs are preferred as the cell type to be employed in the in vivo critically sized defect mouse model, with substantial literature supporting the implantation of hASCs in immune competent mice.

Cell cultures prepared according to the present invention may be gauged using measurable metrics, such as Alk Phosphatase, cellular alignment and morphology, cellular density, and/or mineralization, to determine their appropriateness for incorporation into the system. For example, cell cultures that would be appropriate for use in the present invention exhibit increased staining for alkaline phosphatase, increased cellular alignment, increased nuclear alignment as well as cellular and nuclear aspect ratios, increased cell density; and increased mineralized nodule formation (which can be assayed by Xylinol Orange staining).

Example 14—Cell Culture Substrate

An automated tracking algorithm was designed to process an image stack of stained nuclei and accurately identify, track, and analyze cell motility over long timescales. In this algorithm, cell nuclei are first segmented using a contour-based approach that incorporated cell merging and division capabilities. Interacting cells (cells that merge or divide) are established by isolating contour profiles with multiple-peak intensities and identifying dual peaks (two cells) that share a parent contour. Following tagging of interacting cells, linking is achieved through the use of a particle tracking approach. After tracking is complete, detailed merging and division events are constructed through analysis of cell interactions and cell tracks are corrected using a customized cost function. Finally, the high-accuracy tracking enabled by the correction of merging and division events is leveraged in quantitative analyses, in which the updated tracks are sent through a series of correlation functions to quantify cell motility behavior, including mean squared displacement (MSD) and velocity autocorrelation.

The tracking code was applied to the study and analysis of cell motility on the complex topography changing wrinkle substrates, which have a high order of anisotropy. Gold-coated substrates with micron-scaled wrinkles were used to investigate the effect of a highly anisotropic topography on cell motility behavior, and those results were compared to cell motility behavior atop gold-coated substrates with a flat topography. Tissue culture polystyrene (TCPS) was used as a control substrate to ensure that the material was not indicative of specific behaviors. Images with poor contrast were acquired, which experimentally enabled cell divisions to occur and analytically tested the robustness of the tracking code. Experiments at three different cell densities were conducted to test the segmentation and merging/division processing of the code as confluence is approached.

Cell culture experiments were conducted by seeding C3H10T1/2 mouse fibroblasts on wrinkled, non-wrinkled, and TCPS substrates. Cells were seeded using a droplet method. Cell solutions with concentrations of 87,500, 175,000, and 262,500 cells per ml were prepared. These densities correspond to increasing cell-to-cell interactions, further testing the capabilities of the developed approach and its ability to process more dense environments. In each case, a 20 µL droplet of cell solution was seeded onto the substrates and samples were then placed in a 37° C. incubator for 2 h to allow for cell attachment. After 2 h, complete growth medium was added and the samples were placed in a 37° C. incubator for an additional 22 h, after which point the cells were stained and prepared for live cell imaging.

Cell tracks were plotted to visualize collective cell motility behavior. Qualitatively, wrinkled trajectories displayed directionality corresponding to the wrinkled direction, while non-wrinkled topographies displayed random trajectories.

Mean squared displacement and velocity profiles were characterized. Mean squared displacement values showed similar motility behavior at short timescales. However, at long time scales, the lowest density exhibited distinct differences in motility behavior. For all wrinkled velocity profiles, a clear separation between x and y correlations indicated preferential migration along the wrinkled direction. For non-wrinkled velocities, this directional motion was not apparent.

The topography changing substrates successfully controlled stem cell morphology. The intent is for this morphological control to be employed to control cell differentiation and cell sheet engineering, such as by taking advantage of the osteogenic potential of two different topographic transitions, namely, the flat to nano-scale wrinked transition and a transition from a flat topography to a square-wave topography of parallel plateaus 15 µm wide spaced 15 µm apart and 5 µm high.

Example 15—In Vivo Assessment

A mouse critically sized defect model may be used for in vivo assessment. For example, a graft may be implanted into a 4 mm defect created in the middiaphysis of the femur of a recipient mouse and secured with an intramedullary pin. Three experimental groups may be examined: the scaffold of the present invention alone, the scaffold in combination with the sleeve of the present invention, and the scaffold in combination with the sleeve and the periosteal sheets of the present invention.

What is claimed is:

1. A method of repairing a bone defect, comprising the steps of:
   positioning a porous foam scaffold comprised of a shape memory polymer configured for expansion in response to a stimulus within said bone defect, wherein said porous foam scaffold has a pore size of 200 to 500 micrometers and a porosity of 79 percent plus or minus five percent;
   applying a stimulus to said scaffold to cause said porous foam scaffold to expand into said bone defect.

2. The method of claim 1, wherein said porous foam scaffold comprises a polymer selected from the group consisting of poly(tert-butyl acrylate/butyl acrylate), poly-DL-lactide, and poly-DL-lactide/polyhedral oligomeric silsesquioxane.

3. The method of claim 1, further comprising the steps of:
   positioning a sleeve comprised of a second shape memory polymer that is configured for radial contraction in response to a second stimulus around said bone defect and said porous foam scaffold;
   applying said second stimulus to contract said sleeve around said bone defect and said porous foam scaffold.

4. The method of claim 3, wherein said sleeve comprises a thermoplastic polyurethane.

5. The method of claim 4, said sleeve includes semi-crystalline polyester fibers.

6. The method of claim 5, wherein the semi-crystalline polyester fibers comprise poly(L-lactic acid).

* * * * *